United States Patent
Smeeton et al.

(10) Patent No.: US 10,139,386 B2
(45) Date of Patent: Nov. 27, 2018

(54) OPTICAL SENSOR FOR FLUID ANALYSIS

(71) Applicant: Sharp Kabushiki Kaisha, Osaka (JP)

(72) Inventors: Tim Michael Smeeton, Oxford (GB);
Edward Andrew Boardman, Abingdon (GB); Jun Mori, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 113 days.

(21) Appl. No.: 15/383,777

(22) Filed: Dec. 19, 2016

(65) Prior Publication Data
US 2017/0097329 A1    Apr. 6, 2017

Related U.S. Application Data

(63) Continuation of application No. 14/464,964, filed on Aug. 21, 2014, now Pat. No. 9,568,458.

(51) Int. Cl.
*G01N 33/18* (2006.01)
*G01N 21/53* (2006.01)
*G01N 21/59* (2006.01)
*G01N 21/85* (2006.01)
*G01N 21/33* (2006.01)
*G01N 21/31* (2006.01)

(52) U.S. Cl.
CPC .......... *G01N 33/188* (2013.01); *G01N 21/33* (2013.01); *G01N 21/532* (2013.01); *G01N 21/59* (2013.01); *G01N 21/85* (2013.01); *G01N 2021/3188* (2013.01)

(58) Field of Classification Search
None
See application file for complete search history.

(56) References Cited

U.S. PATENT DOCUMENTS

| | | | |
|---|---|---|---|
| 3,853,407 A | 12/1974 | Dewey, Jr. |
| 3,895,661 A | 7/1975 | Praglin |
| 3,935,463 A | 1/1976 | Jacobsen |
| 4,014,612 A | 3/1977 | Atwood |
| 4,587,518 A | 5/1986 | King |

(Continued)

FOREIGN PATENT DOCUMENTS

| | | |
|---|---|---|
| AT | 408488 B | 12/2001 |
| DE | 3324606 A1 | 1/1985 |

(Continued)

OTHER PUBLICATIONS

Office Action for Corresponding Japanese Application No. 2017-510423 dated Dec. 12, 2017 and its English translation.

*Primary Examiner* — Edwin Gunberg
(74) *Attorney, Agent, or Firm* — Renner Otto Boisselle & Sklar

(57) ABSTRACT

A sensor for measuring a concentration of a particular ion, molecule or atom in a fluid includes a sample handling portion for providing at least some of the fluid, a first photo-detection device, and a first light source. The first photo-detection device is configured to measure a power of light incident thereon, and the first light source includes a solid-state light emitting device. The first light source is configured to emit light having a wavelength less than 240 nanometers incident on the fluid provided by the sample handling portion, and the first photo-detection device is configured to receive light having passed through the fluid.

19 Claims, 9 Drawing Sheets

(56) References Cited

U.S. PATENT DOCUMENTS

| | | | |
|---|---|---|---|
| 4,781,456 A * | 11/1988 | Nogami | G01J 3/427 |
| | | | 356/320 |
| 5,436,459 A * | 7/1995 | Koch | G01N 21/39 |
| | | | 250/373 |
| 6,876,487 B1 | 4/2005 | Marshall | |
| 9,179,516 B2 | 11/2015 | Meijer | |
| 2005/0133724 A1 | 6/2005 | Hsieh | |
| 2006/0198761 A1* | 9/2006 | Tokhtuev | G01N 21/251 |
| | | | 422/82.05 |
| 2007/0135694 A1 | 6/2007 | Sato et al. | |
| 2007/0138401 A1 | 6/2007 | Tokhtuev et al. | |
| 2009/0166520 A1* | 7/2009 | Tuli | G01V 9/00 |
| | | | 250/253 |
| 2010/0327755 A1 | 12/2010 | Meijer | |
| 2011/0019183 A1 | 1/2011 | Ukon et al. | |
| 2011/0242539 A1* | 10/2011 | Christensen | G01J 1/02 |
| | | | 356/440 |
| 2012/0061579 A1 | 3/2012 | Wynn | |
| 2013/0015362 A1 | 1/2013 | Hooper et al. | |
| 2013/0100977 A1 | 4/2013 | Smeeton et al. | |
| 2015/0153272 A1 | 6/2015 | Ehring et al. | |

FOREIGN PATENT DOCUMENTS

| | | |
|---|---|---|
| DE | 4407332 A1 | 9/1985 |
| DE | 19902396 A1 | 6/2002 |
| DE | 10228929 A1 | 1/2004 |
| DE | 102011081317 A1 | 4/2012 |
| EP | 0670485 A1 | 9/1995 |
| GB | 2269895 A | 2/1994 |
| JP | 52-115268 | 9/1977 |
| JP | 4-260404 | 9/1992 |
| JP | 5-240789 | 9/1993 |
| JP | H0868755 A | 3/1996 |
| JP | 08-285834 | 11/1996 |
| JP | 9-304272 | 11/1997 |
| JP | 2000206039 A | 7/2000 |
| JP | 3335776 B2 | 8/2002 |
| JP | 2005091095 A | 4/2005 |
| JP | 4109596 B2 | 4/2008 |
| JP | 2010-117133 | 5/2010 |
| JP | 2013-088822 | 5/2013 |
| WO | WO 0146656 A1 | 6/2001 |
| WO | WO 03067228 A1 | 8/2003 |
| WO | WO 2004003524 A1 | 1/2004 |
| WO | WO 2013/178770 A1 | 12/2013 |

* cited by examiner

OPTICAL SENSOR FOR FLUID ANALYSIS

RELATED APPLICATION DATA

This application is a continuation of U.S. application Ser. No. 14/464,964 filed on Aug. 21, 2014, the contents of which is hereby incorporated by reference in its entirety.

TECHNICAL FIELD

This invention relates to optical sensors using solid-state light sources for fluid analysis applications.

BACKGROUND ART

It is important to be able to measure the concentration of species such as molecules or ions in a fluid in a range of technical fields, including for environmental, health and industrial applications. There is, therefore, a strong demand for reliable, low-cost and long lifetime sensor technologies which can be used to measure the concentration of species such as chemical molecules and ions in fluids.

For example, there is a significant demand for sensors to measure the concentration of the nitrate ion ($NO_3^-$) in drinking water and waste water. The nitrate ion is suspected of being harmful to humans and animals and there are limits placed on the concentration of nitrate ions found in potable water, such as 10 mg/liter nitrate ion as nitrogen ($NO_3^-$—N) concentration in the United States and 50 mg/liter nitrate ion ($NO_3^-$) concentration in Europe. It is important to be able to confirm that the nitrate ion concentration in drinking water is below these limits, especially when reservoirs, rivers and ground water may be contaminated by nitrate ions from fertilisers used in agriculture. Wastewater with a high nitrate ion concentration which is discharged into the environment can cause eutrophication, such as algal blooms, resulting in oxygen depletion (hypoxia) in the water and having a negative impact on the ecosystem. There are typically limits in place on the maximum concentrations of nitrate ions in water which is released back into the water cycle, and therefore there is a demand for effective nitrate ion sensor technologies to analyse this water.

A growing area of interest in ion sensing is in the food production industries of aquaculture and hydroponics. In aquaculture excessive levels of ammonium ions, nitrite ions or nitrate ions can have an adverse effect on the growth of fish leading to a decrease in yield. In hydroponics the concentration of ions, particularly the nitrate, phosphate and potassium ions, in the feed stock supplied to the crops must be maintained at an optimum level in order to maximise yields. The current prevailing method in both these industries is to send water samples for laboratory analysis to determine the ion concentrations. This entails waiting for the analysis to be conducted and the results returned, meaning that monitoring is not continuous and immediate adjustment of an ion concentration towards a target value is not always possible.

Technologies to address the need for the continuous monitoring of ions are known in the prior art, including ion-selective electrodes (ISEs) and optical sensors. In the case of nitrate ion sensing, the optical approach may be preferable because ISEs suffer from drift, require frequent recalibration and have relatively short lifetimes.

Existing optical nitrate ion sensors rely on the direct absorption of ultraviolet light by the nitrate ion, typically light with a central wavelength less than 240 nm. The concentration of nitrate ions can then be calculated from the measured transmission of light through the sample and the well-known Beer-Lambert law: $A=\varepsilon \cdot c \cdot L$ where A is the absorbance given by $$A = -\log_{10}\left(\frac{\text{transmitted light power}}{\text{initial light power}}\right),$$

$\varepsilon$ is the molar absorption coefficient of the nitrate ion, c is the concentration of the nitrate ion, and L is the path length through the sample. The nitrate ion molar absorption coefficient spectrum is known in the prior art and is plotted in FIG. 1. The absorption of wavelengths greater than approximately 240 nm is very small and the absorption increases sharply as the wavelength is reduced below 240 nm. In order to generate a wavelength of light which is strongly absorbed by the nitrate ion (i.e. a wavelength less than approximately 240 nm) a xenon lamp or a deuterium lamp is typically used in the optical nitrate ion sensors found in the prior art. Both xenon and deuterium lamps emit broadband radiation (i.e. radiation including a range of wavelengths) which includes ultraviolet radiation with wavelengths less than 240 nm. Other lamps have also been suggested, such as a mercury-iodine lamp which emits at 206 nm.

Numerous features are taught in the prior art which seek to improve the accuracy of nitrate ion concentration measurements which use absorption of ultraviolet light. For example, a reference measurement can be used to determine the intensity of the light source in order to establish the correct value for "initial light power" in the Beer-Lambert equation. Ways to do this include splitting the beam so that a reference channel is created (e.g. DE4407332C2), spreading the beam so that a portion of the beam does not pass through the analyte and combining with a moveable beam block to obstruct either the measurement path or the reference path (e.g. AT408488B), or inserting and removing a reference material into the beam path (e.g. U.S. Pat. No. 3,853,407, WO03067228A1).

The measurement of the absorption by nitrate ions at multiple wavelengths is also detailed in the prior art. For example, the use of two or more wavelengths of ultraviolet light to determine the dependence of absorption on wavelength is described in DE3324606C2 and JP4109596B2.

If the nitrate ion concentration in a fluid is determined from the absorption of light with wavelength in the range 200 nm-240 nm, the measurement may be inaccurate if other components in the fluid (in addition to nitrate ions) also absorb the same light by an unknown amount. This inaccuracy may be reduced using a second absorption measurement at a different wavelength. In one example, patents including GB2269895B, JP3335776B2 and DE10228929A1 disclose the use of an absorption measurement in the wavelength range 250 nm-300 nm to compensate for absorption caused by organic molecules. In a second example, methods of accounting for light scatter caused by suspended particles (turbidity) are detailed in patents DE19902396C2, JP4109596B2 and JP3335776B2, which use transmission at 830 nm, transmission at 633 nm and a direct measurement of the scattered light respectively.

A nitrate ion concentration measurement using two different path lengths to improve accuracy is included in patents DE19902396C2 and AT408488B. The use of a variable measurement path length is included in GB2269895B. This can be used to obtain a preferred strength of the absorption for a particular nitrate ion concentration and thereby extend the measurable concentration range of the sensor. Additionally, patent application JP2000206039A instructs that a longer wavelength should be used for the absorption measurement when high concentrations of the nitrate ion are present.

Two different detector configurations for nitrate ion sensors are described in the prior art. In a first configuration the broadband light from a UV lamp (e.g. xenon lamp or deuterium lamp) propagates through the analyte water; the light which propagates through the water is then filtered using a bandpass filter which transmits light with a range of wavelengths distributed around a central wavelength; and the light which propagates through the filter is then detected using a photodetector (e.g. DE3324606C2). Bandpass filters for suitable deep UV wavelengths (200 nm-240 nm) have relatively poor performance and high cost. For example, commercially available filters with a transmission bandpass full width at half maximum (FWHM) of 10 nm have a maximum transmission of less than 20%. A further disadvantage is that matched filters may be necessary where a reference channel and a measurement channel which operate at the same wavelength are used. In a second configuration the broadband light from a UV lamp propagates through the analyte water; the light which propagates through the water is then detected using a spectrometer which determines the spectrum of the transmitted light (i.e. the intensity of light as a function of wavelength) (e.g. AT408488B). This second configuration can provide high accuracy nitrate ion concentration measurement but spectrometer components have high cost.

The prior art further includes nitrate ion sensors which are either immersion sensors or in-line sensors. An immersion sensor is one where the analyte water to be measured is supplied to the sensor by immersing part or all of the sensor in the water. An in-line sensor is one where the analyte water is continuously supplied to the sensor and the water is measured as it flows between an inlet and an outlet.

The prior art includes devices for optical sensors in other fields (other than for sensing nitrate ions) which use light sources other than xenon and deuterium lamps. Patent application DE102011081317A1 presents an alternative light source for in-line sensor applications. One or more solid-state ultraviolet sources are held in a housing and emit in the wavelength range 240 nm to 400 nm and may have a FWHM within the range 10 nm-20 nm. A method of driving multiple sources by pulsing them in turn to obtain measurements is included.

Another example of the use of a solid-state light source for sensor applications is patent application US20130015362A1 which discloses the use of a frequency-doubled laser as the light source of a sensor for detecting the presence of particles such as bacteria. Neither DE102011081317A1 nor US20130015362A1 provide a device suitable for measuring the concentration of nitrate ions in water. Optical nitrate ion sensors using solid-state light sources have not been found in the prior art.

In summary, optical nitrate ion sensors in the prior art suffer from several disadvantages. For example, the use of deuterium or xenon lamps, which are complex gas-filled light sources, results in nitrate ion sensors which have high cost, occupy large volumes ($\geq 2{,}000$ cm$^3$), require high voltage ($\geq 400$ V) driving electronics, have high power consumption (between 2 W and 7.5 W depending on the exact source and configuration used), require warmup-time before a measurement may be made and necessarily include inefficient and high cost bandpass filters or a high cost spectrometer. These disadvantages present a significant barrier to a much more widespread deployment of nitrate ion sensing.

SUMMARY OF INVENTION

An apparatus in accordance with the present invention can determine the concentration of an ion, molecule or atom in a fluid while overcoming one or more of the disadvantages in the prior art. The apparatus in accordance with the present invention includes a solid-state light emitting component (e.g., a light-emitting diode (LED) or a laser diode (LD)) as a light source and uses a measurement of the transmittance of light with wavelength less than 240 nm to determine the concentration of an ion, molecule or atom present in the fluid. The apparatus may be used to measure the concentration of nitrate ions in water.

In operation, light from the light source with power $P_1$ is made incident on the analyte and the transmitted light power $P_2$ is measured using a photodetection means. The transmittance of the light $P_2/P_1$ allows the absorbance of the light by the ions, molecules or atoms (referred to hereafter as "the target") to be determined and the concentration of the target may be determined using the Beer-Lambert law. The power $P_1$ may optionally be determined using a second photodetection means.

A more accurate measurement of the absorbance of the target may be obtained by accounting for the other optical losses of the sensor system. These may be determined from a calibration process.

In accordance with one aspect of the present invention the wavelengths emitted by the light source are stabilised against variation in the operating condition of the light source to improve the reliability of the concentration calculation. This aspect of the invention is particularly beneficial where the absorption coefficient of the target varies significantly for small changes in the wavelength of the light emitted by the light source, e.g., for the nitrate ion in water between 205 nm and 240 nm. This problem arises due to solid-state light emitters exhibiting a central emission wavelength which shifts depending on operating conditions (e.g., temperature, driving current/voltage). Nitrate sensors in the prior art use broadband lamps and bandpass filters and therefore are not affected by shifts in wavelength of light used to determine absorbance. However, this unreliability can be a significant problem for nitrate ion sensors using an absorption of light with wavelength less than 240 nm emitted by a light source including a solid-state emitter. This source of error has not been found in prior art describing the use of solid-state ultraviolet light sources with wavelength in the range 240 nm to 400 nm for absorption measurements (e.g. DE102011081317A1).

In one aspect of the present invention the central wavelength of the light emitted by the light source is determined by a direct or indirect method to improve the reliability of the sensor device. This reduces the impact of errors introduced by wavelength variation of the light source by allowing the appropriate absorption coefficient $\varepsilon(\lambda)$ to be determined and used in the concentration calculation.

In one aspect of the present invention the light emitted by the light source has a narrow spectral bandwidth and thereby provides a sensor device which is easy to manufacture, easy to calibrate and which has good reliability. When the absorption coefficient of the target varies for different wavelengths in the light emitted by the light source an undesirable nonlinear dependence of absorbance on concentration of the target occurs. This is particularly a problem for a sensor device configured to determine the concentration of nitrate ions in water, where the dependence of absorbance on nitrate ion concentration is highly non-linear unless the spectral bandwidth of the light is less than 2 nm. A substantially linear dependence of absorbance on the concentration of the target is a significant advantage because use of a nonlinear correction factor is not required to calculate the concentration of ion, molecule or atom of interest in the analyte. Therefore, the calibration process for the sensor is simplified and high accuracy may be achieved over a wide concentration range.

An apparatus in accordance with another aspect of the invention uses a light source including a solid-state light emitter and one or more frequency-converting elements. The frequency-converting element converts the frequency of the light emitted by the solid-state light emitter, for example by second harmonic generation process. This aspect is particularly advantageous when the frequency conversion results in shorter wavelength light than that emitted by the solid-state light emitter. In this case the magnitude of the shift in the central emission wavelength of the light source caused by variation of operating conditions is smaller than the shift of the central wavelength of the solid-state light emitter. The magnitude of this shift in the central emission wavelength of the light source may be further reduced if the frequency-converting element is configured to preferentially frequency-convert light with a particular range of wavelengths. The inclusion of a frequency-converting element in the light source may therefore provide improved reliability for an apparatus in accordance with the invention. This advantage of using a frequency-converted light source has not previously been appreciated in the prior art and is particularly beneficial for use in a sensor device configured to determine the concentration of nitrate ion in water.

A second advantage gained by using a frequency-converting element in the light source is that the light source provides light with a central wavelength which has a small spectral bandwidth. This second advantage of using a frequency-converted light source has not previously been appreciated in the prior art. A narrow spectral bandwidth is advantageous so as to provide a substantially linear dependence of absorbance on concentration of the target and thereby provide a sensor device which is easy to manufacture, easy to calibrate and which has good reliability.

In a further aspect of the present invention, one or more additional, or secondary, light sources may optionally be included in the sensor device to be used to measure the transmittance of light with one or more different wavelengths through the system and analyte. The transmittance of the one or more additional wavelengths may be used to determine a property of either the analyte or the system which may affect the transmittance of the light emitted by the primary light source. This allows a more accurate value of the absorbance caused by the target to be found and hence a more accurate value of the concentration of the target to be obtained.

An apparatus, such as a sensor device, according to aspects of the invention provides significant advantages over sensor technologies described in the prior art, in particular for a sensor to measure the concentration of nitrate ions in water.

Sensors for monitoring nitrate ion concentration in water using solid-state light emitters have not been found in the prior art. The use of solid-state light emitters as described herein provides significant improvements over the sensors in the prior art. For example, nitrate ion sensors in accordance with the present invention may have lower cost, smaller size, improved robustness, improved reliability and reduced power consumption.

Furthermore, the use of measures to control or monitor the wavelength of light generated by solid-state light sources, as disclosed herein, is useful in solving the unreliability of a sensor device configured to measure the concentration of a target where $d\varepsilon(\lambda)/d\lambda$ is large. This problem is identified for the first time herein and is important for the specific challenge of measuring the concentration of nitrate ions in water owing to the natural instability in emission wavelength from solid-state light emitters depending on their operating conditions. The significantly improved linearity of the dependence of absorbance on concentration, owing to the use of solid-state light emitters with narrow spectral bandwidth (e.g., laser diodes), further provides more accurate and more easily manufactured sensors.

The use of frequency-converting elements in a light source for the sensor device further enhances the advantages of the invention. In particular, the unanticipated advantage of decreasing the error and unreliability caused by variation in the wavelength of solid-state light emitters, and the advantage of further reducing the spectral bandwidth and thereby providing very high linearity in the dependence of absorbance on concentration. A system in the prior art for measuring absorption due to particles (US20130015362A1) includes use of SHG to provide light for an absorption measurement. However, a sensor device produced according to this prior art is unsuitable for measuring the concentration of nitrate ions in water. In particular, a device according to US20130015362A1 does not provide any control over the wavelength of the light generated by frequency-doubling or the spectral bandwidth of the emitted light. Both of these features are shown here to be important aspects of a viable nitrate ion sensor device.

There has been a longstanding demand for a new, lower cost, sensor technology to determine the concentration of nitrate ions in water. There has been no significant progress in this field for at least 15 years prior to the present invention. This demand is met by the apparatus in accordance with the present invention, thereby enabling practical use of nitrate ion sensing in much wider range of applications including point-of-use identification of unsafe drinking water (e.g., for water drawn from wells), widespread environmental monitoring, improving the productivity of food production in aquaculture and hydroponic food production and wastewater treatment.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

In the annexed drawings, like references indicate like parts or features.

DESCRIPTION OF REFERENCE NUMERALS

Figure 1:
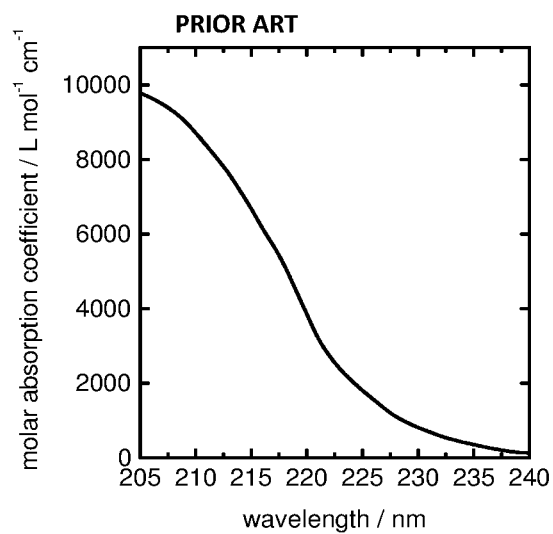
FIG. 1 shows the molar absorption coefficient spectrum of the nitrate ion in water as found in the prior art.

1. Target
2. Analyte
3. Light source
4. Solid-state light emitter
5. Light
6. Incident light
8. Transmitted light
9. Photodetection means
10. Window
11. Window
12. Analyte-handling means
20. Photodetection means
21. Light
22. Partially reflective mirror
23. Controller
24. Wavelength-stabilising element
25. Temperature control means
26. Wavelength filter
27. Temperature sensing means
28. Mirror
30. Light source
31. Frequency-converting element
32. Light
33. Filter
34. Light
35. Light
36. Light
37. Mirror
38. Mirror
39. Transmitted light
40. Light source
41. Solid-state light emitter
42. Temperature control means
43. Temperature sensing means
46. Photodetection means
47. Photodetection means
48. Partially reflective mirror
49. Incident light
50. Window
51. Light
52. Photodetection means
60. Water source
61. Water point of use
62. Controller
63. Alarm
64. Concentration adjusting means
65. Additional sensor device
100. Sensor device according to this invention
101. Sensor device according to this invention

DETAILED DESCRIPTION OF INVENTION

A sensor device in accordance with the present invention can determine the concentration of an ion or molecule in a fluid while overcoming disadvantages of sensors in the prior art. The sensor device in accordance with the present invention includes a solid-state light-emitting component (e.g., a light-emitting diode (LED) or a laser diode (LD)) as a light source and uses a measurement of the transmittance of light with wavelength, $\lambda$, less than 240 nm to determine the concentration of an ion or molecule present in a fluid. The device may be used to measure the concentration of nitrate ions in water.

Figure 2:
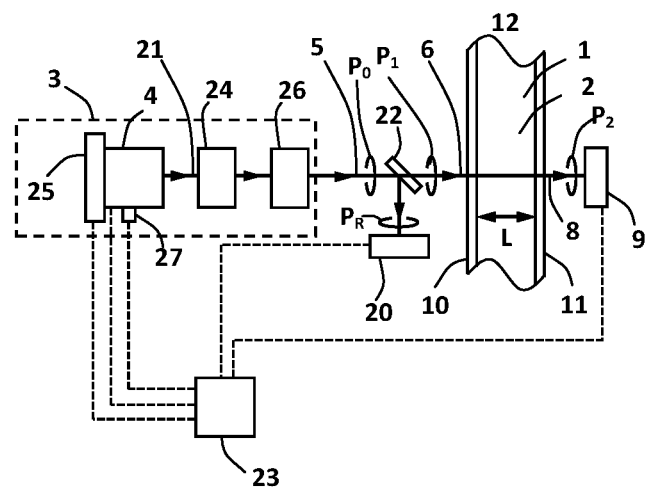
FIG. 2 shows an exemplary sensor device according to an aspect of the invention.

An exemplary sensor device according to an aspect of the invention is illustrated in FIG. 2. The sensor device is configured to determine the concentration of a target 1 in an analyte 2. The target 1 may be one or more type of ion, molecule or atom or any combination of these. A light source 3, including a solid-state light emitter 4, emits light 5 including one or more wavelengths less than 240 nm which are at least partially absorbed by the target 1. Some or all of the light 5 emitted by the light source is incident on, and propagates through, an analyte 2. The light which is incident on the analyte is referred to as the incident light 6 and has power $P_1$. The light propagates through a known distance, L, of the analyte. A fraction of the light is absorbed by any of the target 1 which is present in the analyte 2. After propagating through the analyte 2, the light is referred to as transmitted light 8 and has power $P_2$. The transmitted light 8 is incident on a first photodetection means 9 which is used to measure a power of the transmitted light 8. The values of $P_1$ and $P_2$ may be used to determine the transmittance of the light $(P_2/P_1)$ and thereby may be used to determine the absorbance of the incident light 6 by the target within the analyte. The concentration of the target in the analyte may then be calculated from the absorbance. Coupling of light between all components may be achieved by free-space propagation or by beam-shaping means such as lenses.

The analyte 2 may optionally be disposed between two windows 10 and 11 which are substantially transmissive at the wavelength of the light 6 (e.g., each window transmits at least 10%, and preferably at least 50% of the light) and arranged such that the incident light 6 is coupled such that it passes through a known distance L of the analyte. The analyte 2 is a fluid (i.e. a liquid or gas). For example the analyte may be water.

The power of the incident light 6 ($P_1$) may be optionally determined using a second photodetection means 20, wherein $P_1$ is proportional to the power of the light incident on the second photodetection means 20. The second photodetection means 20 may be located within the light source 3, for example detecting a power of light 21 emitted by the solid-state light emitter 4 within the light source 3. Alternatively, the second photodetection means 20 may be located outside the light source 3, detecting a power of light 5. Optionally an optical component such as a partially reflective mirror 22 may act on the light 5 (for example located between the light source 3 and the analyte 2) and arranged to couple a fraction of the light 5 towards the second photodetection means 20 (this exemplary configuration is shown in FIG. 2). An advantage of including the second photodetection means 20 is that it may be used to identify fluctuations in the power of the light 5 emitted by the light source 3, and thereby enable more accurate measurement of the transmittance of the light.

Alternatively, $P_1$ may be determined from the operating conditions of the light source 3 (for example, the electrical current and/or voltage supplied to the light source 3), and a known dependence of $P_1$ on the operating conditions of the light source 3.

The output from the first photodetection means 9 is used to determine the absorbance, A, by the target 1 of the incident light 6 caused by passing through known distance, L, of the analyte 2. The transmittance of the light ($P_2/P_1$) depends on all optical losses experienced by the light during propagation through the sensor device. Examples of optical losses include reflection or absorption losses at windows (10, 11), scattering losses caused by the analyte (for example due to turbidity) and absorption losses within the analyte (for example due to absorption by the target or by other ions, molecules or atoms in the analyte). The value of $P_2/P_1$ may be described as:

$$\frac{P_2}{P_1} \approx T_A \times \prod_{i=1}^{i=n} T_i$$

wherein $(1-T_A)$ is the fraction of light absorbed by the target in the analyte such that the absorbance by the target is $A=-\log_{10}(T_A)$, and $(1-T_i)$ (where i=1 to n) is the fraction of light lost by each of the n other causes. For example, if the dominant losses are due to reflection and absorption by a first window ($T_1 \approx 0.94$), scattering within the analyte ($T_2 \approx 0.98$), absorption by organic molecules in the analyte ($T_3=0.90$) and reflection and absorption by a second window ($T_4 \approx 0.95$), then n=4 and:

$$\frac{P_2}{P_1} \approx T_A \times \{0.94 \times 0.98 \times 0.90 \times 0.95\}.$$

The values of $T_i$ may be known for a particular sensor device (for example from a calibration process). Some or all of the values of $T_i$ may be determined during operation of the sensor device through separate measurement means. Accordingly, the absorbance, A, of the target may be determined from the measurement of the transmittance of the light $P_2/P_1$. Using the absorbance, A, known distance, L, and known molar absorption coefficient $\varepsilon(\lambda)$ for the target 1 at the one or more wavelengths ($\lambda$) of the incident light 6, the concentration of the target 1 in the analyte may be determined.

The sensor device may optionally include a controller 23 which receives inputs from the first photodetection means 9 and optionally from the second photodetection means 20. The controller 23 may use these inputs to determine the absorbance, A, and further may use algorithms to determine the concentration of the target 1. For example, the controller 23 may include a microcontroller/microprocessor and other electronic circuits. The controller 23 may further include an electrical current generating means which supplies an electrical current to any part of the light source 3, including the solid-state light emitter 4.

In an aspect of the invention the solid-state light emitter 4 may be one or more LEDs or one or more laser diodes which emit light 21 with a central wavelength which is less than 240 nm. Preferably the central wavelength of the light is greater than 200 nm. The use of a solid-state light emitter provides significant advantages over the lamps with bandpass filters used in sensors in the prior art, for example, greater robustness, longer lifetime, lower power consumption and smaller size.

Throughout this disclosure numerical values of wavelength are the wavelength of the light propagating through air with a refractive index approximately equal to one. LEDs and laser diodes typically emit light with a range of wavelengths distributed around a central wavelength. For example, the central wavelength may be equal to the center of a Gaussian function that has been best fit to the emission spectrum of the light using a conventional least-squares error method.

In an aspect of the invention the central wavelength ($\lambda_c$) of the light 5 emitted by the light source 3 is stabilised against variation in the operating condition of the light source, for example so that $\lambda_c$ varies by less than ±4 nm, preferably by less than ±2 nm and most preferably by less than ±1 nm, from a starting value, and thereby provides a sensor device with good reliability. A variation in the operating condition of the light source may include a variation in the ambient temperature, the temperature of the light source, the electrical current and/or the voltage supplied to the light source. This aspect of the invention is particularly beneficial to obtain reliable operation of a sensor device that is configured to determine the concentration of a target for which the absorption coefficient ($\varepsilon(\lambda)$) of the target varies significantly for small changes in the wavelength of the light (i.e. $d\varepsilon/d\lambda|_{\lambda_c}$ has a large positive or large negative value), such as for wavelengths similar to the wavelength of an "absorption edge" in the absorption coefficient spectrum of the target, or for wavelengths on the edge of an "absorption peak". This is particularly important when the target is the nitrate ion and the analyte is water such that the sensor device is configured to measure the concentration of nitrate ions in water, and the central wavelength is between approximately 205 nm and 240 nm. In this case $d\varepsilon(\lambda)/d\lambda$ is a large negative value for wavelengths between 205 nm and 240 nm, $d\varepsilon(\lambda)/d\lambda$ is a very large negative value of less than approximately $-200$ liters·mol$^{-1}$cm$^{-1}$nm$^{-1}$ for wavelengths between 207 nm and 227 nm and $d\varepsilon(\lambda)/d\lambda$ is an exceptionally large negative value of approximately $-664$ liters·mol$^{-1}$cm$^{-1}$nm$^{-1}$ for a wavelength of approximately 220 nm.

Figure 3:
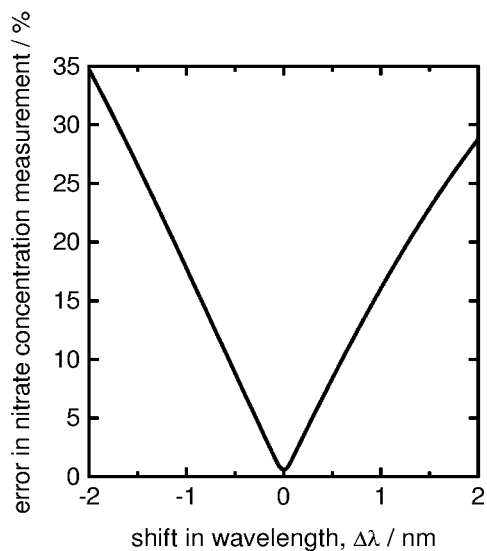
FIG. 3 shows the error introduced into a nitrate ion concentration measurement due to a shift in the central wavelength of the light emitted by the light source.

If the central wavelength of the light 5 emitted by the light source 3 is not stabilised against variation then the sensor device may become unreliable because the absorption coefficient ($\varepsilon(\lambda)$) which is used to determine concentration from the measured absorbance is inappropriate. For example, if the light 5 emitted by the light source 3 is expected to have a central wavelength $\lambda_c$, a calculation of concentration from an absorbance may assume an absorption coefficient of $\varepsilon(\lambda_c)$ (for clarity in this paragraph the example assumes that the light 5 has single wavelength $\lambda_c$ such that the bandwidth of the light 5 is negligibly small, but in general this may not be the case). However, if, owing to a shift in wavelength of the light emitted by the solid-state light emitter 4, the light 5 emitted by the light source 3 has a central wavelength $\lambda_c+\Delta\lambda$, the calculation of concentration will be erroneous because an absorption coefficient of $\varepsilon(\lambda_c+\Delta\lambda)$ should more properly be used. For example, in the case of measurement of the concentration of the nitrate ion in water, FIG. 3 shows the relative error in nitrate ion concentration measurement caused by a shift in central wavelength by $\Delta\lambda$ from a starting central wavelength of 220 nm. The errors are large even for small values of $|\Delta\lambda|<1$ nm. This source of measurement error does not apply to nitrate ion sensors in the prior art and has not been identified previously. Nitrate ion sensors in the prior art provide light with wavelength less than 240 nm by combining broadband lamps (e.g. xenon lamps or deuterium lamps) with a bandpass filter, wherein the filter transmits a range of wavelengths of light with wavelength less than 240 nm. The range of wavelengths of light transmitted by these bandpass filters are not significantly affected by changes in operating conditions (for example, changes in ambient temperature). Therefore, nitrate ion sensors in the prior art are not affected by shifts in wavelength of the light used to determine absorbance.

Solid-state light sources may exhibit a significant shift in the wavelength of the emitted light due to a change in operating conditions, such as temperature of the light source, electrical current and/or the voltage supplied to the light source. For example, for lasers and LEDs, in the case of temperature variation, a typical shift in central wavelength of emitted light is 1 nm/10° C. In a further example, in the case of changes in electrical current supplied to the light source, the central wavelength of emitted light may vary by several nm over a range of typical operating currents. Therefore, sensors configured to determine the concentration of a target from the transmittance of light with wavelength less than 240 nm emitted by a light source 3 including a solid-state light emitter 4 and for which $d\varepsilon(\lambda)/d\lambda$ of the target has a large positive or large negative value for wavelengths less than 240 nm may be rendered unreliable if there is any variation in the operating condition of the light source 3.

This unreliability is a significant problem for nitrate ion sensors using transmittance of light with wavelength less than 240 nm emitted by a light source 3 including a solid-state light emitter 4.

This source of error has not been found in prior art describing use of solid-state UV light sources with wavelength in the range 240 nm to 400 nm for absorption measurements (e.g. DE102011081317A1).

To solve this problem, in an aspect of the present invention the central wavelength of the light 5 emitted by the light source 3 is stabilised against variation in the operating condition of the light source. According to an aspect of the present invention, possibilities to achieve this include, but are not limited to, one or any combination of the following:

1) The use of an optional wavelength stabilising element 24. A wavelength stabilising element 24 reduces variation in the central wavelength of light emitted by the solid-state light emitter 4 due to variation in operating condition. For example, a wavelength stabilising element may be a surface diffraction grating, volume Bragg grating, other diffraction grating or dichroic mirror which returns a portion of the light emitted by the solid-state light emitter 4 back towards the solid-state light emitter 4 and preferentially promotes emission of a particular wavelength by the solid-state light emitter 4, thereby reducing the variation in the wavelength of the emitted light when the operating conditions are changed compared with the case that the wavelength stabilising element was not present. For example, if the solid-state light emitter 4 includes a laser diode and the wavelength stabilising element 24 is a surface diffraction grating, the surface diffraction grating may be configured to form an external cavity diode laser configuration (e.g. Littrow configuration or Littmann-Metcalf configuration). This is an exemplary configuration shown schematically in FIG. 2. An optical element such as a lens may be disposed between the solid-state light emitter 4 and the wavelength stabilising element 24 (this optical element is not shown in FIG. 2). The wavelength stabilising element 24 is not necessarily located between the solid-state light emitter 4 and the analyte 2, as in the example in FIG. 2.

2) The use of optional temperature control means 25. A temperature control means 25 maintains the temperature of the solid-state light emitter 4 within a specified range, and thereby reduces the variation in wavelength of the light emitted by the solid-state light emitter due to a change in operating conditions. For example, the temperature of the solid-state light emitter 4 may be maintained within a specified range of ±1° C. from a central temperature so that the wavelength of the emitted light varies less when the ambient temperature and/or the electrical current supplied to the solid-state light emitter 4 vary than would be the case without the temperature control means 25. The temperature control means 25 may receive controlling input from the optional controller 23. The exemplary configuration shown schematically in FIG. 2 includes a temperature control means 25.

3) The use of an optional wavelength filter 26. A wavelength filter 26 is more transmissive to light with one or more wavelengths within a range than it is to wavelengths outside of that range. Therefore, the wavelength filter 26 reduces the variation in wavelength of light after propagation through the filter, even if the wavelength of light emitted by the solid-state light emitter changes due to a change in operating conditions. Examples of suitable wavelengths filters include band-pass filters, short-pass filters, long-pass filters, diffraction gratings and prisms.

In an aspect of the invention the central wavelength of the light 5 emitted by the light source 3 is determined by a direct or indirect method and thereby provides better reliability of the sensor device. This feature of the invention may be used to reduce the impact of errors which were illustrated in FIG. 3. Even if the wavelength of the light emitted by the solid-state light emitter 4 changes due to a change in operating conditions, the appropriate absorption coefficient $\varepsilon(\lambda_c)$ may be used to determine the concentration of the target from the absorbance if the central wavelength, $\lambda_c$, is determined. According to an aspect of the current invention, possibilities to achieve this include, but are not limited to, one or any combination of the following:

1) The use of optional temperature sensing means 27. The temperature sensing means may measure a temperature of the solid-state light emitter 4 or the light source 3. The temperature of the solid-state light emitter 4 or the light source 3 may be used as an indirect measure of the central wavelength of light emitted by the solid-state light emitter 4. For example, the temperature of the solid-state light emitter 4 may be compared with a known or estimated variation of emission central wavelength with temperature. For example, the temperature sensing means may be a thermocouple or thermistor.

2) The use of an electrical current sensing means. A current sensing means may determine the electrical current supplied to the solid-state light emitter 4. The known value of electrical current supplied to the solid-state light emitter 4 may be used as an indirect measure of the central wavelength of light emitted by the solid-state light emitter 4. For example, the electrical current supplied to the solid-state light emitter 4 may be compared with a known or estimated variation of emission central wavelength with electrical current.

3) Measurement of the central wavelength of the light emitted by the solid-state light emitter 4 by spectrophotometric means.

Any means used to directly or indirectly determine the central wavelength of the light may provide input to the optional controller 23 and thereby be used to improve the accuracy of the concentration of the target determined from the absorbance. For example, the temperature measured by the temperature sensing means may be provided as an input to the controller 23.

In an aspect of the invention the light 5 emitted by the light source 3 has a narrow spectral bandwidth, for example a spectral bandwidth less than 2 nm and preferably approximately 1 nm, and thereby provides a sensor device which is easy to manufacture, easy to calibrate and which has good reliability. This aspect of the invention is particularly important to obtain reliable operation of a sensor device that is configured to determine the concentration of a target for which the absorption coefficient ($\varepsilon(\lambda)$) of light by the target varies significantly for small changes in the wavelength of the light.

The spectral bandwidth of the light is a measure of the range of wavelengths which are present in the light. In this disclosure the spectral bandwidth is defined as the full width at half maximum (FWHM) of the spectrum of the light. For example the spectral bandwidth is equal to the FWHM of a Gaussian function that has been fitted to the spectrum of the light using a conventional least-squares error method.

When the absorption coefficient ($\varepsilon(\lambda)$) of the target varies for different wavelengths in the incident light 6 an undesirable non-linear dependence of absorbance on the concentration of the target occurs. The more the absorption coefficient varies within the spectral bandwidth of the incident light 6, the increasingly non-linear the response will be. This is particularly a problem for a sensor device configured to determine the concentration of nitrate ion in water. In this case the value of $\varepsilon(\lambda)$ of the nitrate ion changes rapidly between wavelengths of 240 nm and 200 nm from a value of $\varepsilon(\lambda=240\text{ nm})\approx 100$ liters·mol$^{-1}$·cm$^{-1}$ to a value of $\varepsilon(\lambda=200\text{ nm})\approx 10{,}000$ liters·mol$^{-1}$·cm$^{-1}$. In this case the dependence of absorbance on nitrate ion concentration is highly non-linear unless the spectral bandwidth of the incident light 6 is less than 2 nm. The non-linearity is apparent from the plot in FIG. 4. This plot shows the dependence of absorbance on nitrate ion concentration for incident light 6 with a central wavelength of 220 nm and spectral bandwidths of 10 nm, 2 nm, 1 nm and 0.1 nm. This plot shows that there is a substantially nonlinear dependence of absorbance on nitrate ion concentration for incident light 6 with a spectral bandwidth of 10 nm. In contrast, the dependence is substantially linear for incident light 6 with a spectral bandwidth of less than 2 nm and in particular for spectral bandwidths of 1 nm or 0.1 nm.

A substantially linear dependence of absorbance on the concentration of the target is a significant advantage because then no nonlinear correction factor is required to calculate the concentration of ion or molecule of interest in the analyte. Therefore, the calibration process for the sensor is simplified and high accuracy may be achieved over a wide concentration range.

According to the invention it is preferred that the spectral bandwidth of the incident light 6 used in the sensor device is less than 2 nm. This provides the significant advantages of linearity over sensors (e.g., nitrate ion sensors) in the prior art. Preferentially a solid-state laser is used as the solid-state light emitter 4, for example a semiconductor laser (e.g. a laser diode) or an optically pumped laser. The use of a laser thus offers advantages over sources such as LEDs which have much larger spectral bandwidths. The use of either LEDs or lasers offers significant advantage over UV lamps (e.g. deuterium lamps or xenon lamps) combined with a bandpass filter, as are found in the prior art. The emission from a laser diode has a very small spectral bandwidth, typically <2 nm, and may sometimes be referred to as "monochromatic". This means that the absorbance of laser light by the analyte is substantially linear with respect to concentration irrespective of the absorption coefficient spectrum of the target. In contrast the emission from an LED typically has a spectral bandwidth of approximately 10 nm-20 nm. The emission from a UV lamp (e.g. deuterium lamps or xenon lamps) combined with bandpass filters found in the sensors in the prior art typically provides a spectral bandwidth of more than 10 nm.

Figure 5:
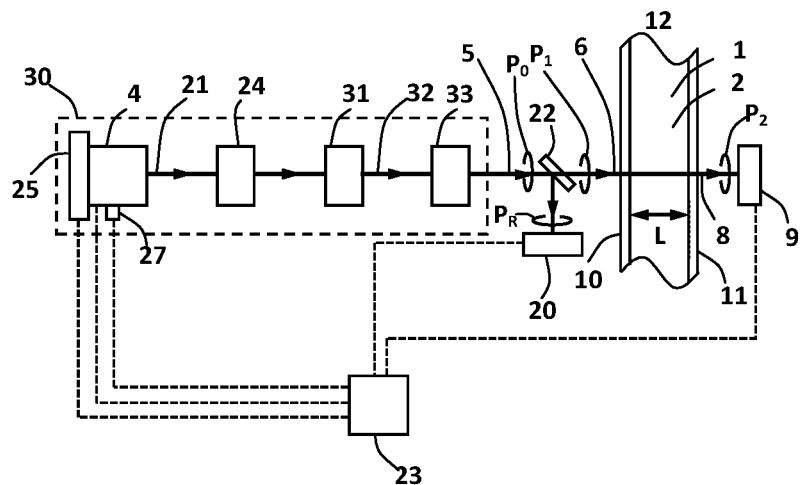
FIG. 5 shows an exemplary sensor device according to an aspect of the invention which includes a frequency-converting element.

A sensor device according to another aspect of the invention is illustrated in FIG. 5. This sensor device shares several features, and many or all of the advantages, of the sensor device described above with reference to FIG. 2. Where components in FIG. 5 are similar to, or have similar function to, components in FIG. 2, they have the same numerical labels and may not be described again. According to this aspect of the invention the light source 30 includes a solid-state light emitter 4 and one or more frequency-converting elements 31. The light 21 emitted by the solid-state light emitter 4 includes light with a first central wavelength ($\lambda_c$). Some or all of this light 21 with a first central wavelength is converted to light with a second central wavelength ($\lambda_c$) by the frequency-converting element. In a preferred example the light 21 is frequency-doubled, for example by a second harmonic generation (SHG) process, by the frequency-converting element 31 so that the second central wavelength is approximately one half of the first central wavelength ($\lambda_c \approx \lambda_c/2$). The light 32 emitted from the frequency-converting element includes light with a second central wavelength less than 240 nm. Preferably the light 32 includes light with a second central wavelength greater than 200 nm. In this example, where the frequency-conversion includes a SHG process, the light 21 includes light with a first central wavelength less than 480 nm and preferably the light 21 includes light with a first central wavelength greater than 400 nm. In alternative examples the light 32 may be converted from the light 21 by other frequency-conversions including, but not limited to: third harmonic generation ($\lambda_c \approx \lambda_c/3$); fourth harmonic generation ($\lambda_c \approx \lambda_c/4$); fifth harmonic generation ($\lambda_c \approx \lambda_c/5$); sum frequency generation; difference frequency generation.

In one example the solid-state light emitter 4 includes a laser diode. For example the solid-state light emitter 4 may include a laser diode emitting light with a first central wavelength in the range between 400 nm and 480 nm, preferably in the range between 420 nm and 470 nm. In another example the solid state light emitter 4 may be a diode pumped solid state laser including a doped laser crystal gain medium.

Optionally the light source 30 may further include a wavelength stabilising element 24. This feature is included in FIG. 5. The wavelength stabilising element 24 may reduce a variation in the wavelength of light emitted by the solid-state light emitter 4 due to variation in operating condition. The wavelength stabilising element 24 may thus reduce a variation in the wavelength of the light 21 with a first central wavelength, which is the "pump" light for the frequency-conversion element 31. Consequently, the wavelength stabilising element 24 has the effect of reducing a variation in the frequency converted light with a second central wavelength in the light 32 because the wavelength of the frequency-converted light is determined by the wavelength of the light 21 (e.g. in the example of a SHG process in the frequency-converting element 31, the wavelength of the light 32 is approximately one half of the wavelength of the light 21). For example, a wavelength stabilising element may be a surface diffraction grating, volume Bragg grating, other diffraction grating or dichroic mirror which returns a fraction of the light emitted by the solid-state light emitter 4 back towards the solid-state light emitter 4 and preferentially promotes emission of a particular wavelength by the light emitter 4, thereby causing the wavelength of the emitted light to vary less when the operating conditions are changed than if the wavelength stabilising element was not present. For example, if the solid-state light emitter 4 includes a laser diode and the wavelength stabilising element 24 is a surface diffraction grating, the surface diffraction grating may be configured to form an external cavity diode laser configuration (e.g., Littrow or Littmann-Metcalf configuration). This is the exemplary configuration shown schematically in FIG. 5. An optical element such as a lens may be disposed between the solid-state light emitter 4 and the wavelength stabilising element 24 (this is not shown in FIG. 5). The wavelength stabilising element 24 is not necessarily located between the solid-state light emitter 4 and the frequency-converting component 31, as in the example in FIG. 5. Furthermore, the frequency-converting element 31 may be disposed between the solid-state light emitter 4 and the wavelength stabilising element 24. In this latter configuration, which is not shown in FIG. 5, the portion of the light which is returned towards the solid-state light emitter 4 and preferentially promotes emission of a particular wavelength of the solid-state light emitter may propagate through the frequency-converting element 31.

Optionally a temperature control means 25 may maintain the temperature of the solid-state light emitter 4 within a specified range, and thereby reduce the variation in wavelength of the light emitted by the solid-state light emitter due to a change in operating conditions. For example, the temperature of the solid-state light emitter 4 could be maintained within a specified range of ±1° C. so that the wavelength of the emitted light varies less when the ambient temperature and/or the electrical current supplied to the solid-state light emitter 4 vary than would be the case without the temperature control means 25. The temperature control means may thus reduce variation in the first and second central wavelengths. The temperature control means 25 may receive controlling input from the optional controller 23.

Optionally, the first central wavelength of the light 21 emitted by the solid-state light emitter 4 and/or the second central wavelength of the frequency-converted light may be determined by a direct or indirect method and thereby provide better reliability of the sensor device. For example by using the temperature sensing means, current sensing means or spectrophotometric means in the same manner as described earlier in the Detailed Description with reference to the sensor device illustrated in FIG. 2.

The light 32 emitted from the frequency-converting element may include light with the second central wavelength and unconverted "pump", or "fundamental", light with the first central wavelength. A filter 33 may be located between the frequency-converting element 31 and the analyte 2. In FIG. 5 the filter 33 is located inside the light source 30 but the filter may be located outside the light source. The filter 33 attenuates the power of light with the first central wavelength by a greater amount than it attenuates the power of light with the second central wavelength. The filter 33 may include one or more bandpass filters. For example, the filter 33 may include one or more mirrors which substantially reflect light with the second central wavelength and substantially transmit light with the first central wavelength, and wherein some or all of the reflected light emerges from the filter as the light 5. Preferably the light with the first central wavelength is significantly attenuated by the filter 33. Preferably the incident light 6 which is incident on the analyte is mostly light with the second central wavelength. For example, the incident light 6 which is incident on the analyte 2 may include a power of light with the second central wavelength which is more than 2, 5, 10, 50, 100, 500 or 1000 times higher than the power of light with the first central wavelength.

The incident light 6 which is incident on the analyte may be used to determine the transmittance of the light ($P_2/P_1$), and thus determine the absorbance of the light by the target and thereby determine the concentration of the target in the analyte as was described for the sensor device shown in FIG. 2 (i.e. with a light source 3 without a frequency-converting element 31).

It is advantageous for a sensor device that is configured to determine the concentration of a target in an analyte from the absorbance of light to include a light source 30 including a solid-state light emitter 4 and one or more frequency-converting elements 31 so that the incident light 6 which is incident on the analyte 2 includes frequency-converted light. It is particularly advantageous when the light 21 with the first central wavelength ($\lambda_c$) is converted to frequency-converted light with a second central wavelength ($\lambda_c$) that is less than the first central wavelength ($\lambda_c < \Lambda_c$), for example when $\lambda_c \approx \Lambda_c/2$.

A first advantage of the light source 30 including one or more frequency-converting elements 31 so that the incident light 6 includes frequency-converted light is that this sensor device (i.e. FIG. 5) can provide a more reliable concentration measurement than a sensor device which determines the concentration of a target in an analyte from the absorbance of light emitted from a light source which includes a solid-state light source but contains no frequency-converting components (e.g. the sensor device described in FIG. 2). This advantage is particularly beneficial to obtain reliable operation of a sensor device that is configured to determine the concentration of a target for which the absorption coefficient ($\epsilon(\lambda)$) of light by the ions or molecules varies significantly for small changes in the wavelength of the light (i.e. $d\epsilon(\lambda)/d\lambda|_{\lambda_c}$ has a large positive or large negative value), such as for wavelengths similar to the wavelength of an "absorption edge" in the absorption coefficient spectrum of the target, or for wavelengths on the edge of an "absorption peak". This is particularly beneficial when a sensor according to the invention is configured to measure the concentration of nitrate ions in water.

Figure 6:
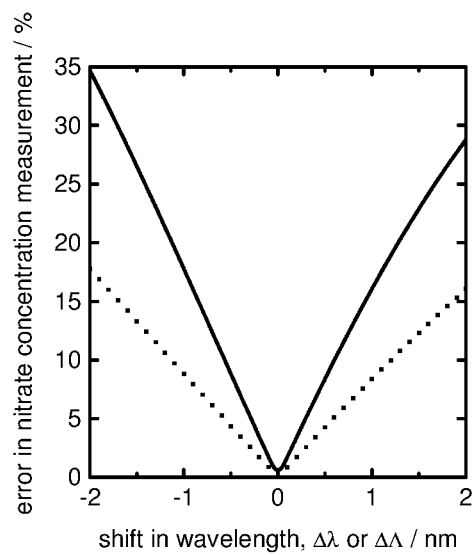
FIG. 6 shows a comparison between the error introduced into a nitrate ion concentration measurement due to a shift in the central wavelength of the light emitted by the solid-state light emitter for a sensor device without frequency-converting components (solid line) and a sensor device with a frequency-doubling element (dotted line).

The first advantage can be understood from FIG. 6. Solid-state light sources may exhibit significant shifts in wavelength of emitted light due to a change in operating conditions. Some details of this behavior were previously described. The disadvantageous consequence of variation in the central wavelength of the incident light 6 which is incident on the analyte 2 was also described, namely that the reliability of the sensor device is reduced because the concentration of the target determined from the absorbance may have large error for small changes in central wavelength of the incident light 6. For the example in which the sensor device is configured to determine the concentration of nitrate ion in water, the plot in FIG. 3 shows that significant errors are introduced by small wavelength shifts ($\Delta\lambda$) from a starting value. In accordance with an aspect of the invention, the wavelength of the light emitted by the solid-state light emitter may be stabilised to reduce the variation. However, some variation of wavelength will still occur and consequently causes error in the nitrate ion concentration determined by the sensor device.

When a frequency converting element 31 is included in the light source 30, such that the second central wavelength ($\lambda_c$) of the frequency-converted light is smaller than the first central wavelength ($\Lambda_c$) of the light emitted by the solid-state light emitter 4, the variation in the second central wavelength is smaller than any variation in the first central wavelength. For example, if the first central wavelength varies by $\Delta\Lambda$, such that $\Lambda_c$ changes to ($\Lambda_c + \Delta\Lambda$), and if the frequency-converted light has a second central wavelength $\lambda_c \approx \Lambda_c/n$, then the variation in the second central wavelength is $\Delta\lambda \approx \Delta\Lambda/n$, such that $\lambda_c$ changes to ($\lambda_c + \Delta\lambda$). For example, when the frequency-conversion is a SHG process such that n=2, the variation in the second central wavelength is approximately one half of the variation in the first central wavelength.

In another aspect of the invention, the variation in the second central wavelength may be further reduced (e.g. to less than one half of the variation in the first central wavelength in the case that the frequency-conversion is a SHG process) if the frequency-converting element 31 is configured to preferentially frequency-convert light with a particular range of wavelengths. This is a further advantage of including a frequency-converting element 31 in the light source 30 in a sensor device. A frequency-converting element 31 may be configured such that a significant amount of frequency-converted light 32 is only generated with wavelengths substantially between $\lambda_1$ and $\lambda_2$ (where $\lambda_1 < \lambda_2$). For example, the frequency-converting element may be configured such that frequency-converted light with wavelengths between $\lambda_1$ and $\lambda_2$ has a power of at least 1% and preferably at least 10% of the maximum power of frequency-converted light obtained for wavelengths between ($\lambda_1 - 0.5$ nm) and ($\lambda_2 + 0.5$ nm), and lower power for wavelengths outside this range. In this case the sensor device will operate under known conditions that the wavelength of the incident light 6 which is incident on the analyte will always lie in the range between $\lambda_1$ and $\lambda_2$, thereby providing high confidence in the appropriate absorption coefficient of the target regardless of the operating conditions of the light source. The value of ($\lambda_2 - \lambda_1$) may be less than 2 nm, less than 1 nm, less than 0.5 nm or less than 0.1 nm. It is preferable that the value of ($\lambda_2 - \lambda_1$) is small.

For example, if the frequency-converting element 31 provides a SHG process, the frequency-converting element may be configured such that a significant amount of frequency-doubled light is only generated from light 21 which has a wavelength in the range between $\Lambda_1$ and $\Lambda_2$, where $\Lambda_1 < \Lambda_2$. Light with these wavelengths would be converted to light with wavelengths of approximately $\lambda_1 \approx \Lambda_1/2$ and $\lambda_2 \approx \Lambda_2/2$ respectively by a SHG process. Therefore, even if the first central wavelength of the light 21 varies to a value significantly lower than $\Lambda_1$ or significantly higher than $\Lambda_2$, the central wavelength of the frequency-converted light will not vary significantly outside the range between $\lambda_1 \approx \Lambda_1/2$ and $\lambda_2 \approx \Lambda_2/2$.

One way that a frequency-converting element may be configured to have suitable $\lambda_1$ and $\lambda_2$ is by ensuring that the frequency-conversion process is not "phasematched" for generation of frequency-converted light with wavelength $\lambda < \lambda_1$ or $\lambda > \lambda_2$. "Phasematching" describes a condition in a frequency-conversion process where light waves of pump light and frequency-converted light remain approximately in phase with one another as they propagate through the frequency-converting element. If a frequency-conversion process is not phasematched then the power of the frequency-converted light may be very low (e.g. less than 10% or less than 1% of the power obtained if the frequency-conversion process is phase matched).

According to an aspect of the invention, the range of wavelengths for which the frequency conversion is phasematched (i.e. the values of $\lambda_1$ and $\lambda 2$) may be controlled by various methods to provide suitable $\lambda_1$ and $\lambda_2$ or suitable values of ($\lambda_2 - \lambda_1$). In a first example of a suitable method, the strength of focussing of the pump light that is incident on the frequency-converting element is chosen to provide suitable $\lambda_1$ and $\lambda_2$ or suitable values of ($\lambda_2 - \lambda_1$). If the pump light is a parallel collimated beam or is loosely focussed in either or both planes of the beam (i.e. the convergence angle of the pump light in one or both planes is small) then ($\lambda_2 - \lambda_1$) may be smaller than ($\lambda_2 - \lambda_1$) obtained when the pump light is tightly focussed (i.e. the convergence angle of the pump light in one or both planes is larger). In a second example of a suitable method, the direction of pump light through the frequency-converting element is chosen to provide suitable $\lambda_1$ and $\lambda_2$ or suitable values of ($\lambda_2 - \lambda_1$). This is particularly suitable for frequency-converting elements in which phase-matching is obtained through so-called "birefringent phase matching". In a third example of a suitable method, the structure of the frequency-converting element is chosen to provide suitable $\lambda_1$ and $\lambda_2$ or suitable values of ($\lambda_2 - \lambda_1$); for example if the length of the frequency-converting element is increased (that is, the length measured parallel to the direction of the pump light) then the value of $(\lambda_2-\lambda_1)$ may be decreased.

Figure 7:
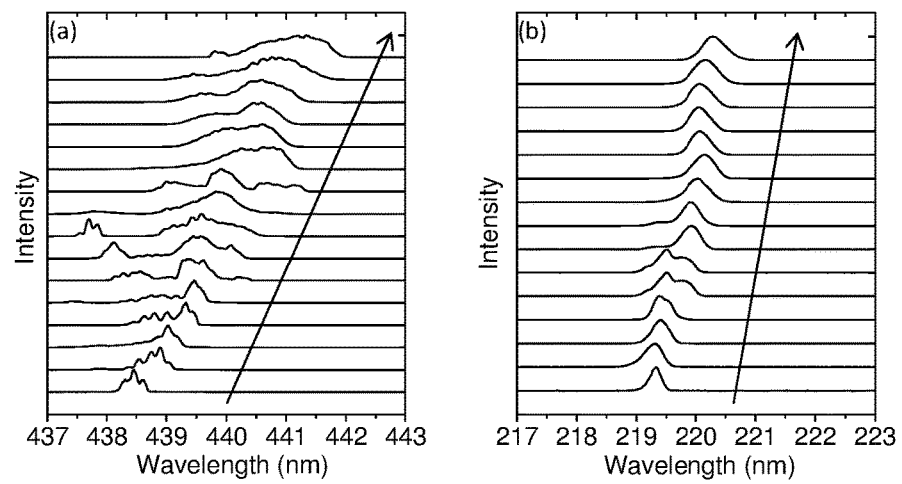
FIG. 7 shows a comparison between the central wavelength of non-frequency-converted light (a) and frequency-doubled light (b) for a range of different driving current conditions. The arrow shows the direction of increasing driving current.

An example of this beneficial effect of including a frequency-converting element in the light source 30 is plotted in FIG. 7. FIG. 7(a) shows the emission spectra from a solid-state light emitter 4 in a light source 30. The solid-state light emitter 4 included a laser diode including $Al_yIn_xGa_{1-x-y}N$ semiconducting materials ($0 \leq y \leq 1$; $0 \leq x \leq 1$; $x+y \lesssim 1$). A temperature control means 25 was applied to the solid-state light emitter 4 which maintained the package containing the laser diode at a temperature of 25° C.±0.1° C. Sixteen spectra are plotted, with vertical offsets between each data. Each spectrum was obtained for a higher electrical current supplied to the laser diode than the spectrum below it. It is apparent that even though a temperature control means 25 was included, the central wavelength of the light emitted by the laser diode varied significantly as the electrical current supplied to the laser diode increased. For example, the central wavelength of the bottom spectrum (lowest current) is approximately 438.4 nm and the central wavelength of the top spectrum (highest current) is approximately 441.0 nm, corresponding to a value of $\Delta\Lambda \approx 2.6$ nm. The arrow shows the direction of increasing electrical current supplied to the laser and indicates the approximate trend in the central wavelength of the light. The light source 30 further included a frequency-converting element 31. The frequency-converting element 31 included a crystal of $\beta$-BaB$_2$O$_4$ configured to provide phasematched type I SHG of the light emitted by the laser diode. FIG. 7(b) shows the spectra of the frequency-converted light generated in the frequency-converting element 31, for the corresponding spectra in FIG. 7(a). It is apparent that the variation in central wavelength of the light in FIG. 7(b) is significantly smaller than the variation in FIG. 7(a). For example, the central wavelength of the bottom spectrum (lowest current) is approximately 219.3 nm and the central wavelength of the top spectrum (highest current) is approximately 220.3 nm, corresponding to a value of $\Delta\lambda \approx 1.0$ nm. The advantageously small variation in wavelength of the frequency-converted light is due both to the effect of the frequency-conversion ($\Delta\lambda \approx \Delta\Lambda/n$, where n=2 in this case) and because in this configuration this particular frequency-converting element preferentially converted light with wavelength of approximately 440 nm to light with a wavelength of approximately 220 nm (more specifically, $\Lambda_1 \approx 439$ nm and $\Lambda_2 \approx 441$ nm; i.e. $\lambda_1 \approx 219.5$ nm and $\lambda_2 \approx 220.5$ nm). Use of a frequency-converting element 31 including a crystal of $\beta$-BaB$_2$O$_4$ is particularly advantageous because it may be configured to provide a small value of $(\lambda_2-\lambda_1)$ due to the phasematching of the SHG process and the values of $\lambda_1$ and $\lambda_2$ for a chosen configuration do not vary significantly if the temperature of the $\beta$-BaB$_2$O$_4$ crystal is changed due to a change in operating conditions.

The use of frequency conversion to provide the incident light 6 which is incident on the analyte 2 thus reduces unreliability caused by a change in the central wavelength of light emitted by a solid-state light emitter due to changes in operating conditions.

Therefore, inclusion of a frequency-converting element provides improved reliability for a sensor device according to the invention, especially providing improved reliability when the operating conditions, such as the ambient temperature of the sensor device varies. This advantage of using a frequency-converted light source has not previously been appreciated in the prior art and is particularly beneficial for use in a sensor device configured to determine the concentration of nitrate ion in water.

For the example that the sensor device is configured to determine the concentration of nitrate ion in water, and the frequency-conversion in the frequency-converting element 31 is an SHG process (i.e. n=2), the improvement according to this aspect of the invention can be seen in FIG. 6. FIG. 6 shows the dependence of error in nitrate ion concentration on shift in wavelength of the solid-state light emitter 4 for a light source 3 which does not include a frequency-conversion (shift in wavelength of solid-state light emitter=$\Delta\lambda$; solid line) and for a light source 30 which does include a frequency-converting element 31 (shift in wavelength of solid-state light emitter=$\Delta\Lambda$; dashed line), where the frequency converting element causes $\Delta\lambda$ to be one half of $\Delta\Lambda$. The error in nitrate ion concentration is approximately halved by the inclusion of a frequency-converting element which includes a SHG process.

A second advantage of the light source 30 including one or more frequency-converting elements 31 so that the incident light 6 includes frequency-converted light is that said light source 30 provides light with a second central wavelength which has a small spectral bandwidth. This second advantage of using a frequency-converted light source has also not previously been appreciated in the prior art. As can be understood from the description above and from FIG. 4, this is advantageous to provide a substantially linear dependence of absorbance on concentration of a target (the target being the nitrate ion in the example of FIG. 4), and thereby provide a sensor device which is easy to manufacture, easy to calibrate and which has good reliability.

A first aspect of the advantage is explained as follows. If the spectral bandwidth of the light emitted by the solid-state light emitter 4 with a first central wavelength ($\Lambda_c$) is $b_1$ (measured in nm of wavelength) then the spectral bandwidth of the light spans wavelengths between $\Lambda_{min} \approx \Lambda_c - b_1/2$ and $\Lambda_{max} \approx \Lambda_c + b_1/2$. In the case that the frequency-conversion is an SHG process, light with these wavelengths is converted to frequency-converted light with a second central wavelength of $\lambda_c$ and a spectral bandwidth of approximately $b_2$ as follows:

$$\lambda_{min} = \lambda_c - \frac{b_2}{2} \sim \frac{\Lambda_{min}}{2} = \frac{\Lambda_c}{2} - \frac{b_1}{4}$$

$$\lambda_{max} = \lambda_c + \frac{b_2}{2} \sim \frac{\Lambda_{max}}{2} = \frac{\Lambda_c}{2} + \frac{b_1}{4}$$

$$\lambda_c \approx \frac{\Lambda_c}{2}$$

Therefore, $b_2 \sim b_1/2$, such that the spectral bandwidth of the frequency-converted light is significantly smaller than the spectral bandwidth of the light emitted from the solid-state light emitter. In general, for a frequency-converting element 31 which generates frequency-converted light with a second central wavelength which is less than the first central wavelength of the light emitted by the solid-state light emitter 4, the spectral bandwidth of the light with a second central wavelength is lower than the spectral bandwidth of the light with the first central wavelength.

A second aspect of the advantage is that the spectral bandwidth of the light 21 may be further reduced by the frequency-converting element 31 if the frequency-converting element is configured to preferentially frequency-convert light with a particular range of wavelengths. As was described above, a frequency-converting element 31 may be configured such that a significant amount of frequency-converted light is only generated with wavelengths between $\lambda_1$ and $\lambda_2$. For example, a frequency-converting element which provides a SHG process may be configured such that a significant amount of frequency-converted light is only generated from light 21 which has a wavelength in the range between $\wedge_1$ and $\wedge_2$. Light with these wavelengths would be converted to frequency-converted light with wavelengths of approximately $\lambda_1 \approx \wedge_1/2$ and $\lambda_2 \approx \wedge_2/2$ respectively by a SHG process. Therefore, even if the spectral bandwidth of the light 21 with a first central wavelength is significantly larger than $\wedge_2-\wedge_1$, the spectral bandwidth of the light 32 with a second central wavelength will not be significantly larger than $\lambda_2-\lambda_1$.

A third aspect of the advantage is that the spectral bandwidth of the light 21 may be further reduced by the frequency-converting element 31 because the efficiency of frequency-conversion of a given wavelength may depend on the power of the light at that wavelength. This may be the case if the frequency-conversion process involves a nonlinear optical process such as SHG. In the case of SHG, for example, wavelengths of light with higher power (e.g. near the central wavelength $\wedge_G$ of a Gaussian-like spectral peak) may be converted with higher efficiency that wavelengths of light with lower power (e.g. with wavelength $\wedge_G+b_G/2$ or $\wedge_G-b_G/2$, where $b_G$ is the spectral bandwidth of the Gaussian-like spectral peak). Consequently the spectral bandwidth of a frequency-converted light may be further reduced compared with the spectral bandwidth of the light emitted by a solid-state light source 4.

Figure 8:
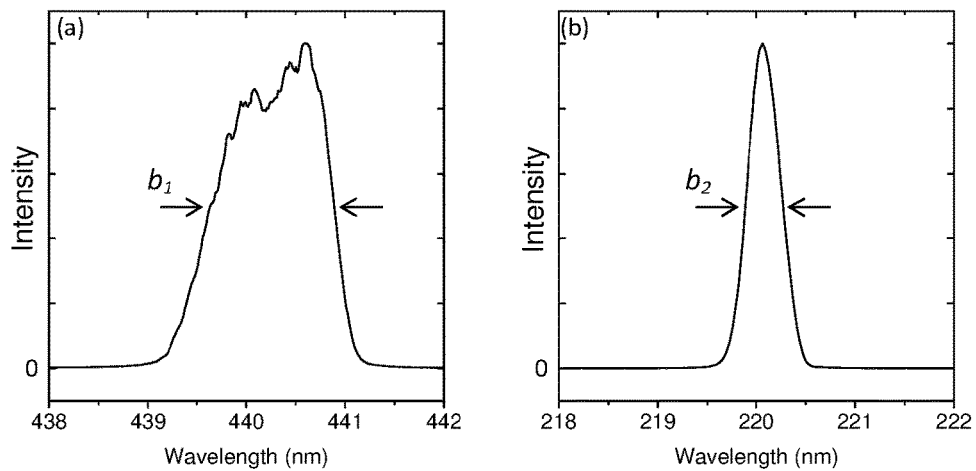
FIG. 8 shows a comparison between the bandwidth of non-frequency-converted light and frequency-doubled light.

An example of this beneficial effect of including a frequency-doubling element in the light source 30 is plotted in FIG. 8. FIG. 8(a) shows the emission spectrum from a solid-state light emitter 4 in a light source 30 (this is the same light source that was described above with reference to FIG. 7). FIG. 8(b) shows the emission spectrum of the light generated in the frequency-converting element 31. The approximate spectral bandwidths are labelled as $b_1$ and $b_2$. The bandwidth of the light generated in the frequency-converting element ($b_2 \approx 0.4$ nm) is significantly narrower than the bandwidth of light emitted by the solid-state emitter ($b_1 \approx 1.2$nm). In this case the laser emitted light with a wavelength of approximately 440 nm but the bandwidth is typical of laser diode emission at many visible and ultraviolet wavelengths.

Figure 9:
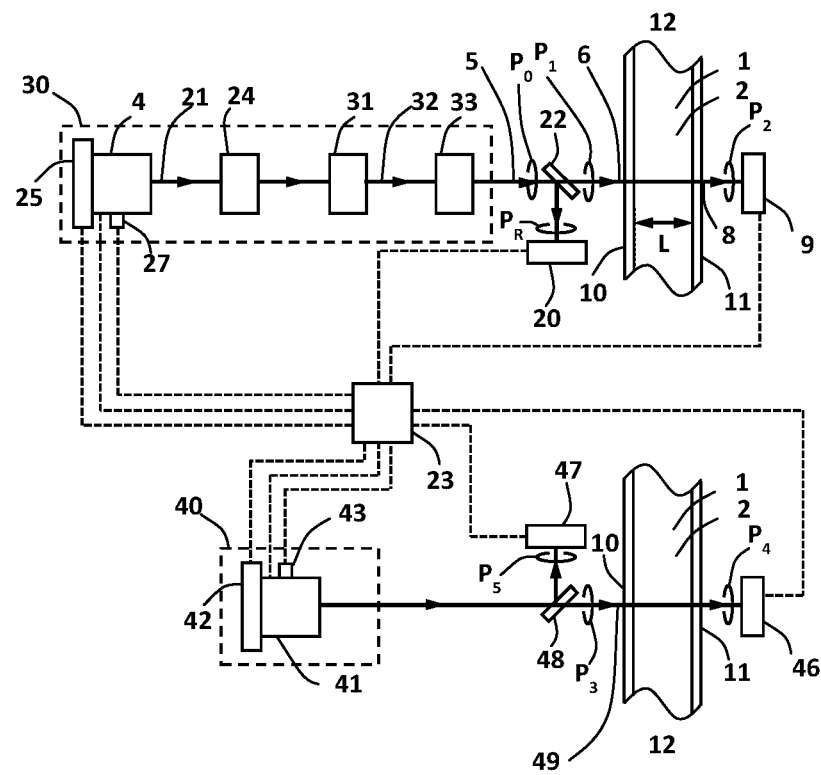
FIG. 9 shows an exemplary sensor device according to an aspect of the invention which includes an additional light source.

In a further aspect of the invention, one or more additional light sources may optionally be included in the sensor device and these may be used to measure the transmittance of light with one or more different wavelengths through the system and analyte. These additional light sources may emit light with any wavelength, including wavelengths greater than 240 nm. The measured transmittance of light emitted by the one or more additional light sources may be used to improve the accuracy with which the concentration of the target 1 is determined from the measured transmittance of the incident light 6 through the analyte (that is, some or all of the light emitted by the light source 3 or 30). A sensor device configured with one additional light source 40 is illustrated in FIG. 9. The sensor device illustrated in FIG. 9 includes several common features with the sensor device illustrated in FIG. 5; features common between the two sensor devices are labelled with the same numerical labels and may not be described again in the following description. In a preferred example the light source 40 includes a solid-state light emitter 41, for example an LED or a laser diode. The light source 40 emits light with a first additional central wavelength. The light source 40 may include a temperature controlling means 42 and/or temperature sensing means 43.

Some or all of the light with a first additional central wavelength that is emitted by the additional light source 40 is incident on an analyte 2 as incident light 49. The light propagates through the analyte, and optional windows 10, 11 and the power of the transmitted light is determined by a third photodetection means 46. The power of the incident light 49 may be determined using a fourth photodetection means 47 which receives a power of light proportional to the power of the incident light 49, optionally via an optical element such as a partially reflective mirror 48.

For example, the transmittance of the light with one or more additional wavelengths may be used to determine a property of either the analyte or the system which may affect the transmittance of the incident light 6, such as the turbidity (light scatter) of the analyte, the concentration of other ions or molecules in the analyte (for example organic molecules) or the cleanliness of the windows 10 and/or 11 (i.e. to determine one or more values of $T_i$). This data may then be used to more accurately determine the concentration of the target 1 by allowing a more accurate value of the absorbance caused by the target 1 in the analyte 2 to be calculated. The data may also be used to determine a second property of the analyte which may also output as a result by the sensor (e.g. the concentration of an ion or molecule other than the target in the analyte). Any number of additional light sources may be included.

For example, in the case that the sensor device is configured to determine the concentration of nitrate ions in water, a first additional light source may be included with a first additional central wavelength between 250 nm and 1000 nm (preferably between 250 nm and 700 nm). The measured transmittance of light with the first additional central wavelength may be used to improve the accuracy of the determination of the absorbance caused by nitrate ions from the transmittance of the incident light 6 ($P_2/P_1$). This may include taking account of phenomena such as absorption at a contaminant layer on one or both of the windows 10 and 11, scattering of light due to turbidity of the analyte 2 and absorption by organic molecules in the analyte 2.

In another example a first additional light source may be included with a first additional central wavelength between 200 nm and 240 nm. The measured transmittance of light with the first additional central wavelength may be used to improve the accuracy of the determination of the absorbance caused by nitrate ions from the transmittance of the incident light 6 by taking account of absorption by nitrite ($NO_2^-$) ions in the analyte 2.

The wavelength of the light 5 emitted by the light source 3 or the light source 30, and the path length 7 through the analyte 2, may be chosen to provide an absorbance by the target which is preferably greater than 0.05 and less than 2.

Preferably the absorbance should be no greater than 2 because above this value the increase in absorbance with concentration may become significantly nonlinear due to overlap of absorption cross-sections, decreasing the accuracy of the measurement. More preferably, the absorbance should be no greater than 1.5. Therefore, the optimal path length L and wavelength of the light 5 may be chosen such that the absorbance is approximately 1.5 for the highest concentration of the target that the sensor device is configured to analyse.

Additional considerations, such as the minimum expected concentration of the target and the minimum or maximum desirable path length can be used to further identify suitable combination of wavelength and path length.

By way of example, consider a sensor device to be used to measure the concentration of nitrate ions in water intended for human consumption to determine whether or not it is safe to drink. The World Health Organisation (WHO) limit for the safe maximum concentration of nitrate ions in drinking water is 50 mg/liter $NO_3^-$ so the sensor device may be expected to give accurate measurements in the range 0 mg/liter $NO_3^-$ to 100 mg/liter $NO_3^-$. A path length of L=5 mm may be preferred for practical considerations, such as low resistance to water flow and ease of window-cleaning while maintaining compactness. For a path length of L=5 mm, a suitable wavelength may be estimated using the Beer-Lambert law and the known wavelength-dependence of the absorption coefficient of the nitrate ion in water. In this case, a suitable wavelength will have an absorption coefficient ε such that A=ε·c·L≈1.5 when c=100 mg/liter and L=5 mm. Therefore, a central wavelength of approximately 225 nm would be a suitable option for the sensor device.

It is noted that there are potentially a wide variety of suitable choices for path length and wavelength for a given concentration range. The above example assumes light 5 with a spectral bandwidth less than 2 nm. If the light 5 has a larger spectral bandwidth the effect of the spectral bandwidth on the overall absorption coefficient to the light 5 may be taken into account.

A sensor device according to aspects of the invention provides significant advantages over sensor technologies described in the prior art, in particular for a sensor to measure the concentration of nitrate ions in water.

No sensors for monitoring the nitrate ion concentration in water using solid-state light emitters have been found in the prior art. The use of solid-state light emitters as taught herein provides significant improvements over the sensors in the prior art which use UV lamps (e.g. xenon lamps or deuterium lamps) with bandpass filters. For example, nitrate ion sensors according to the current invention may have lower cost, smaller size, improved robustness, improved reliability and reduced power consumption. Furthermore, the use of measures to control or monitor the wavelength of light generated by solid-state light sources, as disclosed in the present invention, is important to solve the unreliability of a sensor device configured to measure the concentration of a target with a large positive or large negative $d\varepsilon(\lambda)/d\lambda$. This problem is identified for the first time herein and is important for the specific challenge of measuring the concentration of nitrate ions in water owing to the natural instability in emission wavelength from solid-state light emitters depending on their operating conditions. The significantly improved linearity of the dependence of absorbance on concentration, owing to the use of solid-state light emitters with narrow spectral bandwidth (e.g., laser diodes), further provides more accurate and more easily manufactured sensors.

The use of frequency-converting elements in a light source for the sensor device further enhances the advantages of the invention. In particular, the unanticipated advantage of decreasing the error and unreliability caused by variation in the wavelength of solid-state light emitters, and of further reducing the spectral bandwidth and thereby providing very high linearity in the dependence of absorbance on concentration. A system in the prior art for measuring absorption due to particles (US20130015362A1) includes use of SHG to provide light for an absorption measurement. However, a sensor device produced according to this prior art is unsuitable for measuring concentration of nitrate ions in water. In particular, a device according to US20130015362A1 does not provide any control over the wavelength of the light generated by frequency-doubling or the spectral bandwidth of the emitted light. Both of these features are shown here to be important aspects of a viable nitrate ion sensor device.

There has been a longstanding demand for a new, lower cost, sensor technology to determine the concentration of nitrate ions in water. There has been no significant progress in this field for at least 15 years prior to the present invention. This demand is met by the present invention, thereby enabling practical use of nitrate ion sensing in much wider range of applications including point-of-use identification of unsafe drinking water (e.g., for water drawn from wells or in municipal water treatment), widespread environmental monitoring, improving the productivity of food production in aquaculture and hydroponic food production and wastewater treatment.

EXAMPLE 1

A first example of the invention is a sensor device for detecting the concentration of nitrate ions in drinking water which uses a solid-state light emitter with wavelength less than 240 nm. The sensor device is configured to measure a maximum concentration of 50 mg/liter $NO_3^-$.

A schematic diagram of the sensor device is shown in FIG. 2. The sensor device includes a light source 3 including a solid-state light emitter 4, which emits light 21, an analyte 2 and analyte-handling means 12 (also referred to as a sample handling portion) including a first window 10 and a second window 11. Some or all of the light 21 is emitted from the light source 3 as emitted light 5. Some or all of this emitted light 5 is incident on the first window 10 as incident light 6 and the light propagates through the first window, through the analyte 2, through the second window 11, and the transmitted light 8 is incident on a first photodetection means 9. The first and second windows are substantially transparent to the light 6. Optionally, a partially reflective mirror 22 which is partially reflective to the emitted light 5 is included to direct a portion of the emitted light 5 towards an optional second photodetection means 20. A controller 23 receives input from the first photodetection means 9 and optionally the second photodetection means 20 and controls the operation of the light source 3.

The solid-state light emitter 4 may be an LED emitting light with a central wavelength in the range 200 nm-240 nm. For example, an LED including $Al_yGa_{1-y}N$ semiconductor material (0≤y≤1) may be configured to emit light with a central wavelength between approximately 210 nm and 240 nm. Preferably the LED includes a light-emitting region including $Al_yGa_{1-y}N$ with 0.6≤y≤1 disposed between a p-doped $Al_aGa_{1-a}N$ layer (0≤a≤1) and a n-doped $Al_bGa_{1-b}N$ with (0≤b≤1). In another example the solid-state emitter may include boron nitride or $Al_cGa_dB_{1-c-d}N$ (0≤c≤1; 0≤d≤1). In the remainder of this first example the solid-state emitter 4 is an LED including $Al_yGa_{1-y}N$ semiconductor material emitting light 21 with a central wavelength of approximately 225 nm. The optical power $P_0$ emitted by the light source is preferably greater than 10 μW otherwise the sensitivity of the first detection means must be high. In this example the light source 3 does not include a wavelength stabilising element 24 or filter 26 shown in FIG. 2.

Figure 17:
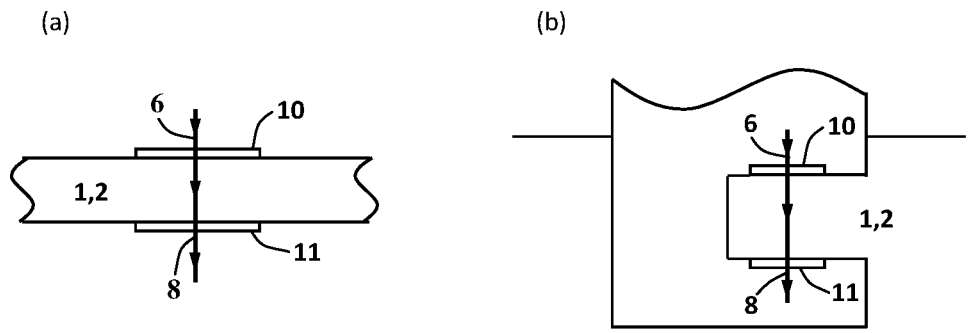
FIG. 17 shows possible arrangements for the analyte-handling means. (a) shows an in-line configuration and (b) shows an immersion configuration.

The first and second windows 10, 11 preferably has have a transmission in the range between 10% and 100% for the incident light 6 (wavelength approximately 225 nm in this example). The windows 10, 11 may include UV-fused silica (UVFS), which has a transmission of ≥90% at λ=225 nm. Other suitable materials for the windows 10, 11 may include quartz, polytetrafluoroethylene (PTFE), fluoropolymers, fluorinated ethylene propylene (FEP), CYTOP and poly (methyl methacrylate) (PMMA). The incident light 6 may pass through the windows 10, 11 at a substantially normal angle of incidence. The distance 7 that the light propagates through the analyte 2 is in the range between 0.1 mm and 100 mm, is preferably in the range between 0.5 mm and 20 mm and most preferably between a lower value of approximately 1 mm and an upper value of approximately 10 mm. In the remainder of this first example the distance is approximately 10 mm. The analyte-handling means 12 may include an analyte inlet and an analyte outlet where the windows 10,11 are disposed between the analyte inlet and the analyte outlet and thereby allows a continuous flow of analyte past the light which propagates between the two windows 10, 11 to provide an in-line sensor as shown in FIG. 17(*a*). For example the analyte handling-means 12 may be a tube (e.g. PVC or another polymer, stainless steel or another alloy) including the windows 10, 11. Alternatively the analyte handling means 12 may provide an immersion sensor as shown in FIG. 17(*b*).

The incident light 6 is incident on the first window 10 with a power $P_1$. The transmitted light 8 is incident on a first photodetection means 9 with a power $P_2$. The photodetection means may include a photodiode which generates an electrical signal proportional to the light incident upon it. For example, the first photodetection means 9 may include a silicon-based photodiode, an $Al_yGa_{1-y}N$-based photodiode ($0 \leq y \leq 1$) or a GaP-based photodiode. Alternatively the first photodetection means 9 may include a silicon-based avalanche photodiode, a photomultiplier tube or a micro-photomultiplier tube. The photodiode may be configured in an electrical circuit so that a potential difference established by the photodiode in response to the absorbed light is monitored as an output. In another example the photodiode may be configured in an electrical circuit so that an electrical current generated in the photodiode in response to the absorbed light is monitored as an output. The output may be conveyed as an input to a controller 23 by either wired or wireless means. The controller 23 includes a microcontroller or microprocessor.

The controller 23 then determines the nitrate ion concentration of the analyte 2 using the input provided by first photodetection means 9. An example of a suitable calculation method is as follows. During a calibration process a measurement is carried out on an analyte containing a known concentration of nitrate ions, preferably deionised water with zero nitrate ion content. The light power in the transmitted light 8 detected by the first photodetection means during this measurement is $P_2'$. The nitrate ion concentration may then be calculated for an unknown analyte according to the power $P_2$ detected by the second photodetection means according to the Beer-Lambert law and the known constants $\varepsilon$ ($\approx 1870$ liters·mol$^{-1}$·cm$^{-1}$ for the nitrate ion for a wavelength of 225 nm) and L (10 mm).

$$c = \frac{A}{\varepsilon \cdot L} \text{ where } A = -\log_{10}\left(\frac{P_2}{P_2'}\right)$$

This calculation may be carried out by the controller 23, using stored values of $\varepsilon$ and $P_2'$ that are appropriate to a particular sensor device. The calibration step may be carried out only once on a representative device and this result applied to similar sensors, the calibration step may be carried out when the sensor is used on an unknown analyte for the first time, or may be repeated as many times as desired.

Figure 4:
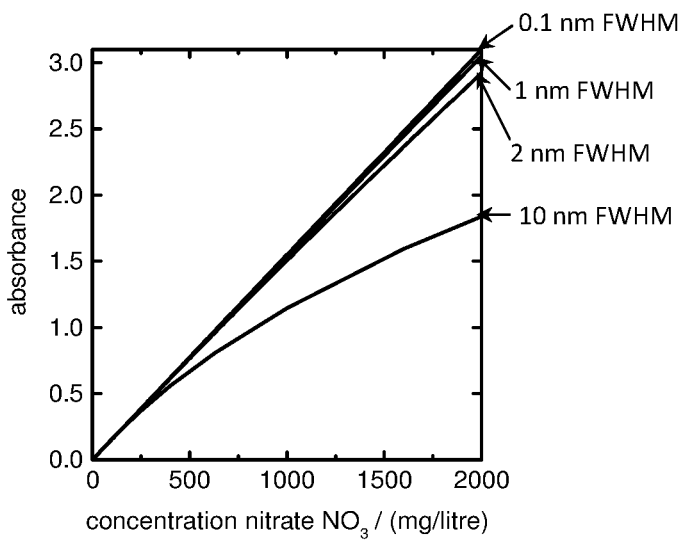
FIG. 4 shows the dependence of the absorbance on the concentration of the nitrate ion in water for light with different spectral bandwidths.

LEDs emit light with a spectral bandwidth which is typically 10 nm-20 nm. This results in the sensor device described above having a nonlinear absorbance response with concentration, as shown in FIG. 4. Therefore, it is advantageous to use a calibration procedure wherein the sensor device is used to measure multiple reference samples with nitrate ion concentrations covering at least the range over which the sensor device is expected to operate. The approximate mathematical dependence of nitrate ion concentration on absorbance may then be determined and used to improve the calculation above, for example the calculation carried out in the controller 23. The concentration of nitrate ions in the analyte may then be calculated from c=f (A) where f( ) is the mathematical dependence of concentration on absorbance. The calibration curve may also be estimated from the known spectrum of the light emitted by the light source 3 and the known variation of absorption coefficient of the nitrate ion on wavelength $\varepsilon(\lambda)$.

Optionally, a partially reflective mirror 22 may be disposed between the light source 3 and the analyte-handling means 12. The partially reflective mirror 22 has a reflectivity in the range 1% to 70% for light with a wavelength of 225 nm. Preferably the reflectivity is between 10% and 50% for light with a wavelength of 225 nm. The light reflected by the partially reflective mirror 22 is incident on a second photodetection means 20. The power of light transmitted through the partially reflective mirror 22 is preferably between 50% and 90% of the power of light incident on the mirror. The power of the light transmitted through the partially reflective mirror 22 is $P_1$ and the power of the reflected light is $P_R$ (referring to FIG. 2). The photodetection means may be a photodiode which generates an electrical signal proportional to the light incident upon it; for example a silicon-based photodiode (similar design considerations as for the first photodetection means 9 described above). The value of $P_1/P_R$ is constant and therefore the measured power $P_R$ may be used to detect and account for fluctuations in the power of the incident light 6 due to fluctuations in the power of the light emitted by the light source 3 in the calculation of the absorbance by the target. For example, if when the analyte is deionised water containing zero nitrate ion content, the power of light incident on the second photodetection means 20 is $P_R'$ and the power of light incident on the first photodetection means 9 is $P_2'$. The nitrate ion concentration in an unknown analyte 2 may then be calculated according to the following equation, which accounts for power fluctuations in the light source 3.

$$c = \frac{A}{\varepsilon \cdot L} \text{ where } A = -\log_{10}\left(\frac{P_2}{P_R} \cdot \frac{P_R'}{P_2'}\right)$$

This calculation may be carried out by the controller 23. The multiple calibration sample method detailed above may be used in combination with the partially reflective mirror 22 and photodiode 20 in a similar manner using this more accurate value for absorbance.

Optionally, the sensor device may include a means for stabilising the wavelength of the light emitted by the light source 3. This may be achieved using an optional temperature control element 25 in thermal contact with the solid-state light emitter 4. The temperature control element is operated such that the temperature of the solid-state light emitter 4 is maintained within a predetermined range over the entire range of expected operating conditions (e.g. ±1° C.). This has the effect of reducing variation in the wavelength of light emitted by the solid-state light emitter 4. The temperature control element may be a Peltier element, one side of which is in thermal contract with the solid-state light emitter 4 and the other side of which is in thermal contact with a heat sink, such that the solid-state light emitter 4 and heat sink are substantially thermally isolated from one another except for through the Peltier element. In other examples the temperature control element may include a fan or liquid heat transfer means (for example using the flow of the analyte to transfer heat towards or away from the solid-state light emitter 4 to maintain a stable temperature). Optionally, a temperature sensing means 27 may be placed in thermal contact with the solid-state light emitter 4. The output from the temperature sensing means 27 may be used by the controller 23 to determine the correct operating conditions for the Peltier element which will keep the temperature of solid-state light emitter 4 within a predetermined range. In another example, a separate electrical circuit such as a "PID" circuit may use the output from the temperature sensing means to determine the correct operating conditions for the Peltier element. The temperature sensing means may be a thermistor, a thermocouple or a semiconductor temperature sensor.

Optionally, if the sensor device includes a temperature sensing means 27, either with or without the temperature control means 25, the temperature of the solid-state light emitter 4 or the light source 3 may be used to indirectly estimate the central wavelength of the light emitted by the solid-state light emitter. For example, a known dependence of the wavelength of the light emitted by the solid-state light emitter on temperature may be used to properly estimate the appropriate absorption coefficient to use in the calculations to determine the concentration of nitrate ions from the absorbance.

Optionally, the sensor device is configured so that little or no ambient light is incident on the first and/or second photodetection means. Ambient light is any light not emitted by the light source 3. Preferably the power of ambient light incident on either photodetection means is less than 10% of the power of the light from the source 3 which is incident on the photodetection means, and most preferably it is less than 1%. The sensor device may be configured with shields which block ambient light from reaching the photodetection means. Preferably the windows 10, 11 are enclosed—for example in a tube—so that ambient light is effectively shielded. The sensor device may therefore be configured such that it does not need bandpass filters to restrict light with some wavelengths from being incident on the photodetection means.

In this first example as described no beam-shaping optical components (e.g. lenses) are used when coupling light between any of the components of the sensor. However, it should be appreciated that one or more optics may be inserted anywhere along the path of any optical beam in order to modify the propagation of the light to improve the performance of the sensor device.

EXAMPLE 2

A second example of the invention is similar to the first example except that the solid-state light emitter 4 includes a laser. Many features are the same as for the first example and these may not be described again. This second example is illustrated in FIG. 2.

The solid-state light emitter 4 may be an optically pumped laser including $Al_yGa_{1-y}N$ materials (0≤y≤1) or a laser diode including $Al_yGa_{1-y}N$ semiconductor materials (0≤y≤1). In the remainder of this second example the solid-state emitter 4 is a laser diode including $Al_yGa_{1-y}N$ semiconductor material emitting light 21 with a central wavelength of approximately 225 nm.

A laser is a preferred choice for the solid-state light emitter 4 in the light source 3 because it emits light with a narrower spectral bandwidth, it provides light with a wavelength which may be stabilised against variation more effectively than an LED, it may provide light which is substantially linearly polarised and it provides light with a high "beam quality" which may readily be formed into a collimated "beam" of light.

The spectral bandwidth of the light 5 emitted by the light source 3 is less than 2 nm and preferably approximately 1 nm. This narrow spectral bandwidth provides a substantially linear dependence of absorbance on the concentration of nitrate ions in the analyte, thereby improving the reliability of the sensor and reducing the complexity of the calibration of the sensor or possibly eliminating the need for calibration altogether.

The inclusion of a laser diode in the light source 3 also enables the use of an additional optional method for stabilising the wavelength of the light emitted by the light source 3 (in addition to the methods described for the first example). This is achieved by placing optional wavelength stabilising element 24 into the path of the optical beam 21 emitted by the laser diode 4. In this example the wavelength stabilising element 24 is a surface diffraction grating, preferably a holographic diffraction grating with a surface including an aluminium layer and with 3600 lines per cm. However, similar performance may be obtained using another diffraction grating, for example a holographic diffraction grating with greater or fewer than 3600 lines per cm, a holographic diffraction grating with a surface including a silver layer or another material layer, a ruled diffraction grating or a volume Bragg grating. Furthermore, similar performance may be obtained using a dichroic mirror, or a bandpass filter combined with another mirror, which reflects a narrow range of wavelengths back towards the solid-state light emitter. A lens is disposed between the solid-state light emitter 4 and the surface diffraction grating. This lens collects the light emitted by the solid-state light emitter into a substantially collimated light beam which propagates towards the surface diffraction grating. The surface diffraction grating is oriented so that the light 21 received from the solid-state light emitter 4 is diffracted through a first (or higher) order diffraction which propagates back towards the solid-state light emitter (i.e. the opposite direction along the same path). This is a "Littrow" external cavity diode laser configuration. The diffracted beam causes the solid-state light emitter to preferentially emit a wavelength similar to the wavelength of light which propagates back towards the solid-state light emitter from the surface diffraction grating, which depends on the orientation of the grating. For example, in the case of a 3600 lines per cm grating, the angle of incidence of the light 21 onto the surface diffraction grating is approximately 23.3° for a wavelength of approximately 220 nm and 23.9° for a wavelength of approximately 225 nm. Thereby the wavelength of the light emission is stabilised against variation in the wavelength which would occur without the action of the surface diffraction grating. The light in the zero-order diffraction from the surface diffraction grating (i.e. the specular reflection from the surface grating) may be coupled towards the analyte and used to determine the absorbance by the target. The portion of the power which is incident on the surface diffraction grating from the solid-state light emitter which is returned towards the solid-state light emitter may be in the range between 5% and 95% but is preferably between 10% and 50%. If a higher portion is returned towards the solid-state light emitter the stabilisation of the wavelength may be improved. This wavelength stabilisation may be combined with other measures described for the first example such as an optional temperature control means 25.

The use of a laser diode as the solid-state light emitter provides a further advantage that the light emitted by a laser diode as a high "beam quality" which may readily be formed into a collimated "beam" of light. The incident light 6 which is incident on the analyte may thus be contained within a small cross-sectional area (measured in the plane perpendicular to the direction of propagation of the light). This provides significant advantages for low cost sensor. The windows 10, 11 may have small cross-sectional area. Some suitable materials for windows which have high transmission for wavelengths between 200 nm and 240 nm are relatively expensive and therefore enabling the use of small windows is a significant advantage. Furthermore, measures to clean the windows 10 and 11 in operation of the sensor device are lower cost and more compact if the windows are small, thereby reducing the overall cost and size of the sensor device. In this example the windows 10 and 11 are approximately 2 mm×2 mm. A further advantage of the high beam quality of the light emitted by a laser diode is that the light may be collected using a lens and focussed to a small spot. Therefore, the first photodetection means (and optionally the second photodetection means) may be small, low cost devices. In this example the first photodetection means is a silicon-based photodiode with a cross-sectional area of less than 1 mm$^2$.

The use of a laser diode as the solid-state light emitter provides a further advantage that the light emitted by the laser diode has a high degree of linear polarisation. Therefore, in this example the windows 10 and 11 are configured so that the incident light 6 is p-polarised and is incident at Brewster's angle at the first window 10 and the first and second windows are parallel to one another. Use of Brewster's angle incidence provides lower reflection losses and thereby increases the power of the light incident on the first photodetection means 9. For windows 10 and 11 made of UV fused silica, the angles of incidence in air is approximately 56°.

EXAMPLE 3

A third example of this invention is now described. The third example is similar to the first and second examples and common features may not be repeated. In this third example, which is illustrated in FIG. 5, deep ultraviolet light in the wavelength range 200 nm-240 nm is generated by frequency-conversion of longer wavelength light emitted by a solid-state light emitter which is a semiconductor laser such as a laser diode.

The sensor device includes a light source 30 in which the solid-state light emitter 4 is a semiconductor laser which emits light 21 that passes through one or more frequency-converting elements 31. The semiconductor laser emits light with a central wavelength between a lower value of approximately 400 nm and an upper value or approximately 480 nm. In this example the semiconductor laser emits light 21 with a central wavelength of approximately 450 nm. The semiconductor laser in this example is a Fabry-Perot laser diode including $Al_yIn_xGa_{1-x-y}N$ semiconductor materials and $Al_y$-$In_xGa_{1-x-y}N$ light-emitting layers (0≤x≤1 and 0≤y≤1), but other types of semiconductor laser may be used including vertical cavity surface emitting laser diodes, DBR laser diodes, and DFB laser diodes, and lasers including other materials may be used. The light emitted by the laser diode is collected by a lens into a substantially collimated light beam which is incident on a wavelength stabilisation element. An example of a suitable lens is a moulded glass aspheric lens with focal length between 2 mm and 5 mm. In this example the wavelength stabilising element 24 is a surface diffraction grating, preferably a holographic diffraction grating with a surface including an aluminium layer and with 3600 lines per cm. However, similar performance may be obtained using another diffraction grating, for example a holographic diffraction grating with greater or fewer than 3600 lines per cm, a holographic diffraction grating with a surface including a silver layer or another material layer, a ruled diffraction grating or a volume Bragg grating. Furthermore, similar performance may be obtained using a dichroic mirror, or a bandpass filter combined with another mirror, which reflects a narrow range of wavelengths back towards the laser diode. The surface diffraction grating is oriented so that the light 21 received from the laser diode (after being collected by a lens) is diffracted through a first (or higher) order diffraction which propagates back towards the laser diode (i.e. the opposite direction along the same path). This is a "Littrow" external cavity diode laser configuration. The diffracted beam causes the laser diode to preferentially emit a wavelength similar to the wavelength of light which propagates back towards the laser diode from the surface diffraction grating, which depends on the orientation of the grating. For example, in the case of a 3600 lines per cm grating, the angle of incidence of the light 21 onto the surface diffraction grating is approximately 50.7° for a wavelength of approximately 430 nm, approximately 52.4° for a wavelength of approximately 440 nm, approximately 54.1° for a wavelength of approximately 450 nm and approximately 55.9° for a wavelength of approximately 460 nm. Thereby the wavelength of the light emission is stabilised against variation in the wavelength which would occur without the action of the surface diffraction grating. The light 21 in the zero-order diffraction from the surface diffraction grating (i.e. the specular reflection from the surface grating) may be coupled into the frequency-converting element 31 using one or more lenses. A suitable lens is a spherical lens with focal length between 5 mm and 200 mm, preferably between 30 mm and 150 mm. Alternatively, a suitable system includes two cylindrical lenses each with a focal length between 5 mm and 200 mm (the focal lengths of the two lenses may be different) wherein the first cylindrical lens focusses light in a first plane and the second cylindrical lens focusses light in a second plane which is perpendicular to the first plane. The portion of the power which is incident on the surface diffraction grating from the laser diode which is returned towards the laser diode may be in the range between 5% and 95% but is preferably between 5% and 20%. If a higher portion is returned towards the solid-state light emitter the stabilisation of the wavelength may be improved. The surface of the laser diode through which the light is emitted may be anti-reflection coated so that the reflection is less than 2%; this may further improve the wavelength stabilisation. However, it is not essential to anti-reflection coat this surface of the laser diode and in this example the surface is not anti-reflection coated.

The frequency-converting element 31 includes a β-$BaB_2O_4$ crystal which is configured to provide phasematched type I SHG of the light emitted by the laser diode. The β-BaB$_2$O$_4$ crystal has a length (measured parallel to the direction of propagation of the light through the crystal) between 1 mm and 20 mm and preferably between 5 mm and 15 mm. The suitable direction of the pump light in β-BaB$_2$O$_4$ to provide phasematched type I SHG and the suitable polarisation orientation of the pump light are known from the prior art. For this example, where the light emitted by the laser diode has a wavelength of approximately 450 nm, the light with wavelength approximately 450 nm should propagate at an angle, θ$_{BBO}$, approximately 63° away from the optic axis of the β-BaB$_2$O$_4$ crystal, and the dominant electric field of the light should be perpendicular to the optics axis. The frequency-converting element 31 converts a portion of the light with central wavelength of approximately 450 nm to light with a central wavelength of approximately 225 nm. The light with a central wavelength of approximately 225 nm preferably has a power of at least 1 μW and more preferably at least 10 μW.

Light 32 including light with the first central wavelength of 450 nm and the second central wavelength of 225 nm propagates out of the frequency-converting element 31. This light is collected by a lens into a substantially collimated light beam. The light 32 is filtered by a filter 33 which reduces the power of the light with the first central wavelength more than it reduces the power of the light with the second central wavelength. Preferably the majority of the light 5 emitted from the filter is light with the second central wavelength. Most preferably at least 90% of the power of the light 5 is light of the second central wavelength. Frequency-conversion (e.g. by SHG) may occur with relatively low efficiency. Therefore, the power of light with the first central wavelength in the light 5 may be less than 0.01%, less than 0.001% or less than 0.0001% of the light with the first central wavelength in the light 32. The filter may include one or more mirrors including a distributed Bragg reflector (DBR) which has high reflectivity to the light with the second central wavelength (R>90% and preferably R>99%) and low reflectivity to the light with the first central wavelength (R<1%). Suitable DBR mirrors may be fabricated using layers of MgF$_2$ and LaF$_3$ on a UV fused silica substrate. The filter may also include a dispersive element, such as a UV fused silica prism (e.g. a Pellin-Broca prism or an equilateral prism), and arranged to spatially separate the λ=450 nm beam from the λ=225 nm beam.

The incident light 6 is incident on the analyte and the transmittance of the light through the analyte is determined using a first photodetection means 9, as for previous examples. Further, the power of the incident light 6 that is incident on the analyte may be determined using a second photodetection means 20 which detects a portion of the light 5 emitted by the light source 3 and may be used to determine fluctuations in the power of the light 5, or by other methods described above for previous examples. The nitrate ion concentration is thus determined as described in the Detailed Description and for the first example.

In the same way as for the second example, the windows 10, 11 are preferably small, with dimensions approximately 2 mm×2 mm measured perpendicular to the direction of propagation of the light 6, thereby exploiting an advantage of the high beam quality of the light with a second wavelength generated in the frequency-converting element. However, yet smaller or larger windows (e.g. 5 mm×5 mm, 10 mm×10 mm or larger still) may be used. In the same way as for the second example the windows 10, 11 may be oriented at Brewster's angle to the p-polarised light with the second wavelength, thereby exploiting the advantage that the light with the second wavelength generated in the frequency-converting element has substantial linear polarisation. Indeed a further advantage of the inclusion of a frequency-converting element 31 in the light source 30 is that the degree of linear polarisation in the frequency-converted light is very high, and higher than the degree of linear polarisation emitted by a typical solid-state light source such as a laser diode. The first and second photodetection means includes a silicon-based photodiode, for example a UV-enhanced silicon photodiode.

Figure 18:
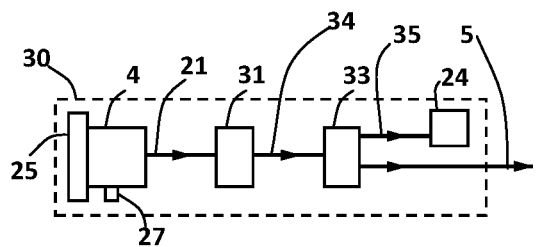
FIG. 18 shows an exemplary light source according to an aspect of the invention.

The light source 30 in the sensor device in this example as described above includes a wavelength stabilising element 24 disposed between the laser diode and the frequency-converting element 31. In an alternative design for the light source 30, the frequency-converting element 31 and a filter 33 may be disposed between the laser diode and the wavelength stabilising element 24. The light source 30 for this alternative design is illustrated in FIG. 18. The light 21 emitted by the laser diode 4, with a first central wavelength, is coupled into the frequency-converting element 31. The light 34 propagating out of the frequency-converting element 31 includes light with the first central wavelength and frequency-converted light with the second central wavelength. The light 34 is split by a filter 33 into light 35 containing at least 10%, and preferably at least 80%, of the light with the first central wavelength and into light 5 containing light with the second central wavelength. The light 35 is incident on a wavelength stabilising element 24, which returns a portion of the light back towards the laser diode along the same path but in the opposite direction through the filter 33 and frequency-converting element 31 (as in the description in this example above). Preferably a lens is disposed between the frequency-converting element 31 and the wavelength-stabilising element 24 to collect divergent light into an approximately parallel beam or to focus the light at the wavelength-stabilising element. The light 5 is used in the sensor device as in the first or second examples. The components in the light sources in FIG. 18 are the same type as described in this example for the light source in FIG. 2, with the exception that the surface diffraction grating used as the wavelength-stabilising element preferably returns at least 60% (most preferably at least 80%) of the light which is incident on it back towards the laser diode.

It is highlighted that throughout the current example the wavelength-stabilising element 24 acts on the light emitted directly from the laser diode and not on the frequency-converted light.

Optionally a temperature control element may be applied to the frequency-converting element 31 to further improve the wavelength stability of the frequency-converted light with the second wavelength in the incident light 5. This is effective because maintaining the temperature of the frequency-converting element within a small range (e.g. ±5° C.) can improve the stability of the wavelength of the light with the second central wavelength which can be obtained by frequency-conversion in the frequency-converting element.

In addition or instead of the wavelength stabilisation using a wavelength stabilisation element 24 as described in this example other measures described for the first example—such as an optional temperature control means 25—may also be included in the current example.

Where a temperature control element 25 is used, as in method 2 of the first example, the temperature control element acts on the solid-state light emitter 4 (a laser diode in this example). One or more of the frequency-converting elements 31 may be in thermal contact with the laser diode. One or more of the optional filters 33 may be in thermal contact with the laser diode.

Alternatively, all wavelength-stabilisation measures may be omitted. In this case the advantageous effect of including frequency-conversion to reduce the effect of variation in wavelength by the solid-state light emitter on the variation of wavelength of the light which is incident on the analyte is exploited. Additionally it may be advantageous to use a temperature sensing 27 means and a known variation of the first central wavelength and/or the second central wavelength with temperature.

As for previous examples, a controller 23 may be included which receives inputs from the first photodetection means 9 and optionally from the second photodetection means 20. The controller 23 may use these inputs to determine the absorbance, A, and further may use algorithms to determine the concentration of the target 1. For example, the controller 23 may include a microcontroller/microprocessor and other electronic circuits. The controller 23 may further include an electrical current generating means which supplies an electrical current to any part of the light source 3, including the solid-state light emitter 4.

The third example was described for a frequency-converting element including β-BaB$_2$O$_4$. The frequency-converting element may include any material capable of generating light with the desired second central wavelength. For example, the frequency-converting component may include one or more of the following: β-BaB$_2$O$_4$, Ba$_{1-x}$B$_{2-y-z}$O$_4$—Si$_x$Al$_y$Ga$_z$ (0≤x≤0.15; 0≤y≤0.10; 0≤0≤0.04; x+y+z≠0), SiO$_2$ (for example, including a periodically twinned structure which provides quasi-phase matched frequency conversion), Al$_y$Ga$_{1-y}$N (0.5≤y≤1) (for example, including a periodic polarisation inverted structure which provides quasi-phase-matched frequency conversion), CsLiB$_6$O$_{10}$, LiB$_3$O$_5$, KBe$_2$BO$_3$F$_2$, Li$_2$B$_4$O$_7$, LiRbB$_4$O$_7$, or MgBaF$_4$ (for example, including a periodic polarisation inverted structure which provides quasi-phasematched conversion).

EXAMPLE 4

A fourth example of this invention is now described. The fourth example is similar to the third example and common features may not be repeated. In this fourth example, which is illustrated in FIG. 9, the sensor device includes a sensor device as described in any of the first three examples (which is now referred to as the "primary" sensor) and one or more additional sensors which are referred to as "secondary" sensors. The measurements from a secondary sensor may be used to improve the accuracy with which the primary sensor determines the concentration of the target in the analyte. A secondary sensor may contain any of the features described for the first three examples. In addition, however, the light source 40 in the secondary sensor may emit light with wavelength greater than approximately 240 nm.

In this fourth example the primary sensor is the same as the sensor device described in the third example; for example the light source 30 is the same as in the third example. One secondary sensor is used in this example and included in FIG. 9. This secondary sensor measures the transmittance of light with a central wavelength of approximately 375 nm through an analyte. The secondary sensor may be used to determine a property of the sensor device (for example, the cleanliness of windows 10, 11) or a property of the analyte (for example, the turbidity of the analyte or the concentration of chemicals other than the target in the analyte). The known or estimated effect of one or more of these properties on the transmittance of light measured by the primary sensor may then be used to improve the accuracy with which the concentration of the target is determined by the primary sensor. More specifically, the secondary sensor may be used to determine a suitable value for a loss, $T_i$ in the primary sensor and thereby take account of this value of $T_i$ when calculating the concentration of the target in the analyte using the output from the primary sensor. This feature is particularly advantageous if $T_i$ varies during deployment of the sensor—for example if the windows 10, 11 become dirty over time or if the turbidity of the analyte varies significantly over time.

In this example the secondary sensor is used to determine a measure of the turbidity of the analyte. The primary sensor and secondary sensor are arranged so that they act upon the same analyte 2. The two sensors may share a single analyte-handling means 12. The sensors may use the same first window 10. The sensors may use the same second window 11.

The light source 40 includes a solid-state light emitter 41 which emits light with central wavelength of approximately 375 nm and in this example is an LED, for example an LED including Al$_y$In$_x$Ga$_{1-x}$N materials where 0≤x≤1 and 0≤y≤1. The light source 40 may further include a temperature controlling element 42 and/or a temperature sensing element 43. The secondary sensor includes a third photodetection means 46 and optional fourth photodetection means 47 to measure the transmittance through the analyte of light emitted by the light source 40 (i.e. the ratio P$_4$/P$_3$, using measurements of P$_4$ and optionally P$_5$, referring to FIG. 9, and where the third and fourth photodetection means operate similarly to the first and second photodetection means 9, 20 in the primary sensor). The third and fourth photodetection means 46, 47 may be photodiodes with similar design considerations as given for the photodetectors in the first example (for example, silicon-based photodiodes).

The concentration of the target 1 (the nitrate ion in this example) in the analyte 2 (water in this example) is determined, for example using a controller 23, using inputs provided by the first, third and optionally second and fourth photodetection means. The calculation may be carried out as in the first example with the following additional steps. The light powers incident on third and fourth photodetection means 46 and 47 during the calibration step described in the first example are P$_4$' and P$_5$' respectively. The analyte used in the calibration step should preferably have negligible turbidity compared with the turbidity of the analyte which will subsequently be analysed by the sensor device; preferably the analyte is deionised water. During analysis of an analyte by the sensor device, the transmittance through the analyte of light with central wavelength approximately 375 nm, $T^{375nm}$, may then be calculated according to measured powers P$_4$ and, optionally, P$_5$ as $$T^{375\ nm} = \frac{P_4}{P_4'} \cdot \frac{P_5'}{P_5}.$$

The value of P$_5$'/P$_5$ may be assumed (e.g. P$_5$'/P$_5$=1) if the optional photodetection means 47 is not included. $T^{375nm}$ may be used to determine the effect of turbidity on the transmittance of light through the analyte in the primary sensor. For example, if the incident light 6 in the primary sensor has a central wavelength of approximately 225 nm, the optical loss in the analyte due to turbidity for light with wavelength 225 nm, $T^{225nm}$, may be determined as $T^{125nm}$=g ($T^{375nm}$), where the mathematical function g( ) may be determined theoretically, empirically or semi-empirically. $T^{225nm}$ may then be used as one of the terms $T_i$ in the equation for the transmitted fraction of the light power in the primary sensor, which includes optical losses not caused by the absorption of light by the target, and which was presented previously in the Detailed Description. For example, the concentration of the target may be calculated using the following equation:

$$c = \frac{A}{\varepsilon \cdot L} \text{ where } A = -\log_{10}\left(\frac{P_2}{P_R} \cdot \frac{P'_R}{P'_2} \cdot \frac{1}{T^{225\,nm}}\right)$$

This advantageously allows the fraction of light in the primary sensor that is lost by one or more causes other than absorption by the target to be quantified when the measurement is made rather than assuming a value, as explained in the Detailed Description. This increases the accuracy of the primary sensor.

The measurement data taken by the sensors need not be taken simultaneously. The introduction of a delay between the measurements is advantageous when the sensors are placed in-line for continuous monitoring and the measurement position of one sensor is downstream of the other. By accounting for the flow rate of the analyte the measurements may be timed such that the same portion of the analyte is in the measurement path of both of the sensors. This makes the system more tolerant to rapidly varying conditions. The flow rate of the analyte may be measured using a flow rate sensor and the information passed to the controller 23, allowing for variable delays between the measurements based on the known flow rate.

Light with wavelength approximately 375 nm has been used in the secondary sensor in this example but other wavelengths may be used. Preferably the wavelength used by a secondary sensor is not strongly absorbed by the target. Other wavelengths may be used to provide a similar correction for other effects. For example, an LED emitting light with wavelength approximately equal to 250 nm may be used to determine a loss in the primary sensor ($T_i$) due to organic compounds present in the system such as in the analyte 2 or on the windows 10, 11. A plurality of secondary sensors may be used to obtain one or more estimates of $T_i$ for the primary sensor and thereby further increase the accuracy of the primary sensor.

EXAMPLE 5

Figure 11:
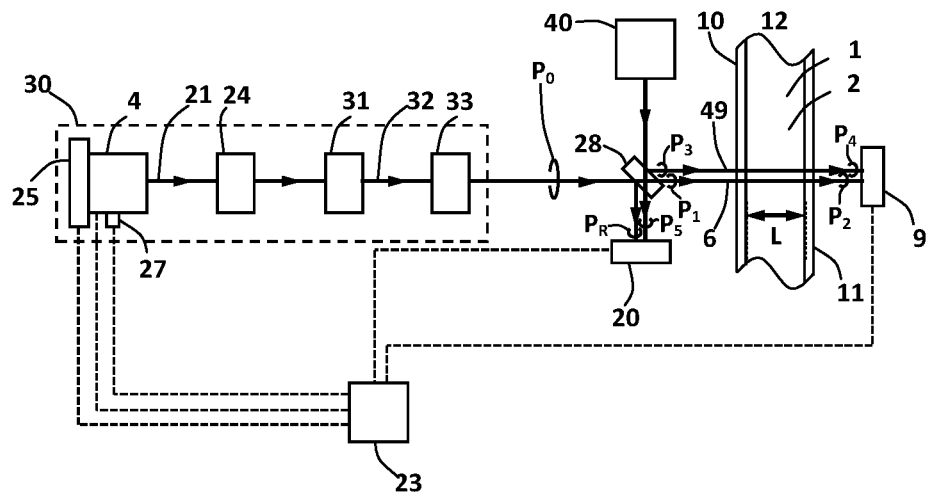
FIG. 11 shows an exemplary sensor device according to an advantageous aspect of the invention which includes an additional light source.

A fifth example of this invention is now described. The fifth example is similar to the fourth example and common features have the same reference numerals and may not be described again. For example, the light sources 30 and 40 are the same as those used in the fourth example. The fifth example is illustrated in FIG. 11. In the sensor device of the fifth example the first photodetection means 9 is used to measure a power of light emitted by the light source 30 which is transmitted through the analyte ($P_2$) and to measure a power of light emitted by the light source 40 which is transmitted through the analyte ($P_4$). The optional second photodetection means 20 is used to measure a power of the light emitted by the light source 30 ($P_R$) and a power of the light source 40 ($P_5$). An optional mirror 28 is configured to direct light emitted by the light sources 30, 40 towards the first and second photodetection means 9, 20.

One possible configuration is illustrated in FIG. 11. In this configuration the mirror 28 reflects light emitted by the light source 40 with a reflectivity in the range between 1% and 99% and preferably in the range between 40% and 90%. The reflected light is the incident light 49, with power $P_3$, which is incident on the analyte and is incident on the first photodetection means 9. Some or all of the light 40 which is not reflected by the mirror 28 is transmitted through the mirror and is incident on the second photodetection means 20, with power $P_5$. The first and second photodetection means 9, 20 thus may deliver the same function as the third and fourth photodetection means 46, 47, respectively, of the fourth example. The mirror 28 reflects light emitted by the light source 30 with a reflectivity in the range between 1% and 99% and preferably in the range between 10% and 60%. The reflected light is incident on the second photodetection means 20, with power $P_R$. Some or all of the light 30 which is not reflected by the mirror 28 is transmitted through the mirror and is the incident light 6, with power $P_1$, which is incident on the analyte and is incident on the first photodetection means 9.

The incident light 6 and the incident light 49 preferably follow similar optical path through the analyte, for example passing through the windows 10, 11 at similar positions. Thus, the primary and secondary sensor systems of the fourth example are combined in the fifth example with fewer components (e.g. the third and fourth photodetection means are not required).

Figure 10:
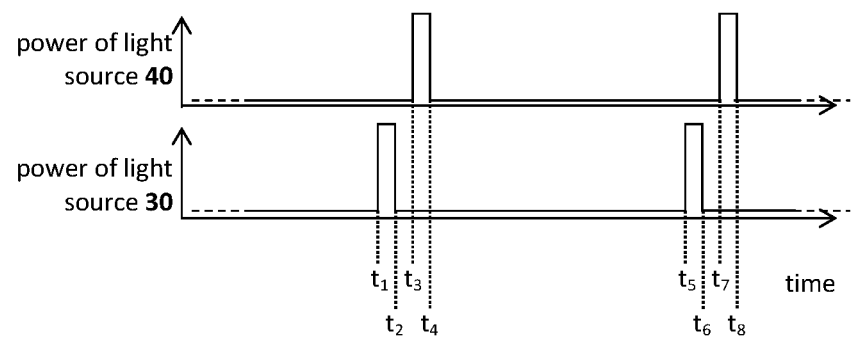
FIG. 10 shows a timeline for two light sources being used in a pulsed operation mode.

For the fifth example it is preferred that the light source 30 and the light source 40 do not emit light at the same time. One possible method of operation is illustrated in FIG. 10 and is described as follows. At a time $t_1$ power is supplied to the light source 30 to switch it to an on state, causing the light source 30 to emit light. At a later time, $t_2$, ($t_2 > t_1$) the supply of power to the light source 30 is stopped and the light source 30 returns to the off-state. In an interval between $t_1$ and $t_2$ a measurement from the first photodetection means 9 is taken ($P_2$) and a measurement from the optional second photodetection means 20 may also be taken ($P_R$). Meanwhile, at a time $t_3$ power is supplied to the light source 40 to switch it to an on state, causing the light source 40 to emit light. At a later time, $t_4$, ($t_4 > t_3$) the supply of power to the light source 40 is stopped and the light source 40 returns to the off-state. In an interval between $t_3$ and $t_4$ a measurement from the first photodetection means 9 is taken ($P_4$) and a measurement from the optional second photodetection means 20 may also be taken ($P_5$). A controller 23 may be used to operate the light sources 30, 40 and receive inputs from the first and second photodetection means 9, 20. The sequence of measurements may be repeated starting at a time $t_5$, as illustrated in FIG. 10.

The measurements taken in the intervals $t_1$ to $t_2$ ($P_2$, $P_R$) and $t_3$ to $t_4$ ($P_4$, $P_5$) are used to calculate the concentration of the ion of interest in the analyte as in the fourth example.

The intervals $t_1$ to $t_2$ and $t_3$ to $t_4$ are preferably arranged such that there is no overlap between them ($t_3 > t_2$ and $t_5 > t_4$) so that the light source 30 and the light source 40 do not operate at the same time. A very wide range of values for $t_1$, $t_2$, $t_3$ and $t_4$ are suitable. For example, the intervals $t_2 - t_1$ and $t_4 - t_3$ may be in the range between 1 μs and 1 s and preferably between 0.1 ms and 50 ms. It is preferable that for $t_3 - t_2$ is less than 1 s. In this fifth example the intervals $t_2 - t_1$ and $t_4 - t_3$ are approximately 20 ms and $t_3 - t_2$ is approximately 2 s.

There are multiple advantages to this fifth example, especially if the incident light 6 and the incident light 49 follow similar optical paths through the analyte. Firstly, the size of the windows 10, 11 of analyte-handling means 12 can be minimised, which may reduce costs. Secondly, in the case where one or both of the windows 10, 11 exhibit increased absorption due to becoming unclean, because of biological growth for example, both the primary light (i.e. from light source 30) and secondary light (i.e. from light source 40) experience the same degree of uncleanliness. This is particularly advantageous in the case where a purpose of the measurement of transmittance of the light emitted by the light source 40 through the windows 10, 11 and the analyte 2 is to determine the effect of uncleanliness of the windows 10, 11 on the transmittance of the light emitted by the light source 30 through the windows 10, 11 and the analyte 2.

Thirdly, if the time between measurements ($t_3-t_2$) is small then the portion of the analyte measured by each sensor will be substantially similar. This minimises any error in the correction factors $T_i$ caused by inhomogeneity in the analyte and hence increases the accuracy of the calculation of the concentration of the ion of interest.

Sensor devices according to this fifth example were used to measure the concentration of nitrate ion in multiple different water sample analytes with both low nitrate ion concentration (less than 100 mg/liter $NO_3^-$) and high nitrate ion concentration (greater than 100 mg/liter $NO_3^-$). For each analyte, the nitrate ion concentration determined by a sensor device as illustrated in FIG. 11 was compared with a measurement obtained using cadmium colorimetry, a well-established method for nitrate ion concentration measurement.

Figure 12:
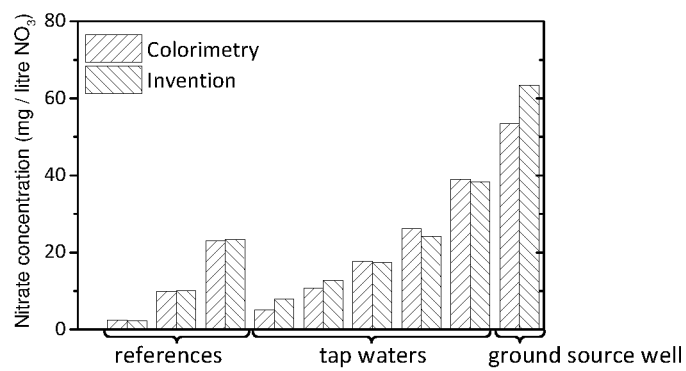
FIG. 12 shows a comparison between results obtained using the sensor shown in FIG. 11 (this invention) and results obtained from cadmium colorimetry on samples with nitrate ion concentrations <100 mg/liter.

The sensor device used for the low nitrate ion concentration analytes was configured so that the light from light source 30 and the light from the light source 40 propagated through the analyte for a distance of L=10 mm. The low nitrate ion concentration analytes included three "references" (deionised waters with known quantities of potassium nitrate added), five "tap waters" (potable tap waters sourced from various locations across Europe) and "ground source well" water taken from a well in the UK. The nitrate ion concentrations measured by colorimetry and by a device including the current invention are shown in FIG. 12. The results from each analyte, obtained using colorimetry and a sensor device as in this example, are plotted as adjacent bars with no gap between them.

The sensor device used for the low nitrate ion concentration analytes was configured so that the light from light source 30 and the light from the light source 40 propagated through the analyte for a distance of L=1 mm. The high nitrate ion concentration analytes included "fish farm" water taken from fish tanks in a land-based seawater fish farm and "hydroponic farm" water taken from the water delivered to plants in a hydroponic farm. The nitrate ion concentrations measured by colorimetry and by a device including the current invention are shown in FIG. 13.

Figure 13:
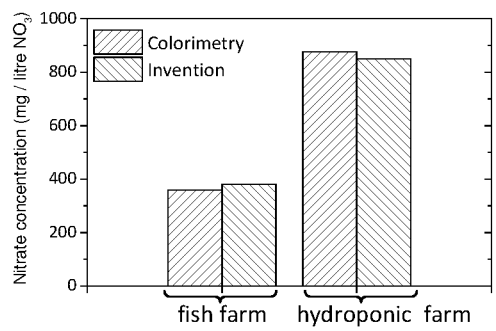
FIG. 13 shows a comparison between results obtained using the sensor shown in FIG. 11 and results obtained from cadmium colorimetry on samples with nitrate ion concentrations >100 mg/liter.

For all of the analytes the nitrate ion concentration determined by the sensor device according to the current invention is in very good agreement with the nitrate ion concentration obtained using cadmium colorimetry (see FIG. 12 and FIG. 13). The excellent correlation between the cadmium colorimetry and the sensor device according to this fifth example demonstrates the efficacy of the current invention.

EXAMPLE 6

Figure 19:
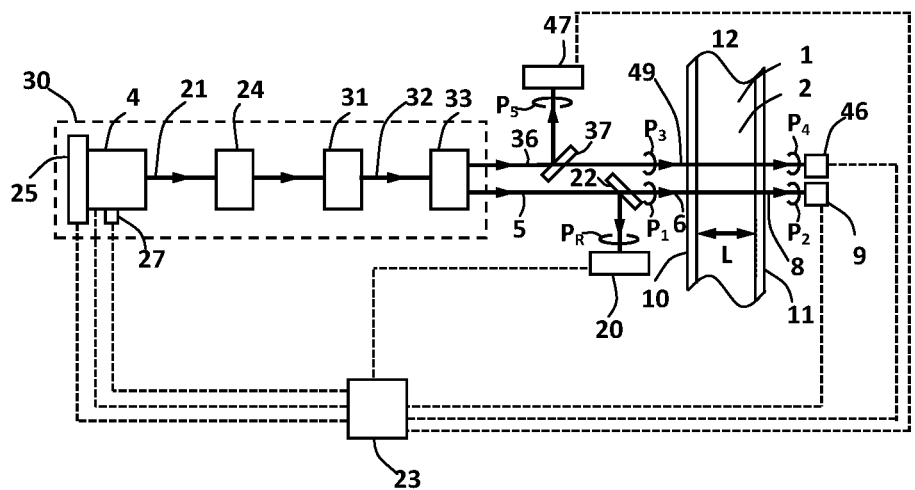
FIG. 19 shows an exemplary sensor device according to an aspect of the invention in which the pump light is used to provide a measurement at a second wavelength.

A sixth example of this invention is now described and is illustrated in FIG. 19. The sixth example shares features with the third, fourth and fifth examples. Common features are indicated by the same numerical labels and may not be described again. The sensor device in the sixth example includes a light source 30 which includes a frequency-converting element 31. The light source 30 is configured so that the light emitted by the light source includes light with the first central wavelength (i.e., some of the light emitted by the solid-state light emitter 4; this is shown as light 36 in FIG. 19.) and light with the second central wavelength (i.e. the frequency-converted light; this is shown as light 5 in FIG. 19). In this sixth example the light 36 is used in a similar way to the light emitted by the light source 40 in the fourth example. By analogy with the fourth example, and reference to FIG. 19, the light 5 is used in a primary sensor (using the first photodetection means 9, an optional second photodetection 20 and an optional mirror 22) and the light 36 is used in the secondary sensor (using the third photodetection means 46, an optional fourth photodetection means 47 and an optional mirror 37). An advantage of this sixth example compared with the fourth example is that the light source 40 is not required.

For this sixth example the light source 30 is the same as the one described for the fourth example, except that the filter 33 is configured to provide both light 36 and light 5. The filter 33 is preferably configured so that the power of the light 36 is greater than 0.01 multiplied by the power of the light 5 and less than 10 multiplied by the power of the light 5. The filter 33 may include one or more mirrors as described for the third example.

Although the light 36 and the light 5 are shown as separate lines in FIG. 19, the light 36 and the light 5 may propagate along substantially the same path. The optional mirror 22 may be configured to reflect light with the second central wavelength more strongly than it reflects light with the first central wavelength so that the light incident on the second photodetection means provides a measure of the power of the light with the second central wavelength. And the optional mirror 37 may be configured to reflect light with the first central wavelength more strongly than it reflects light with the second central wavelength so that the light incident on the fourth photodetection means provides a measure of the power of the light with the first central wavelength.

EXAMPLE 7

Figure 20:
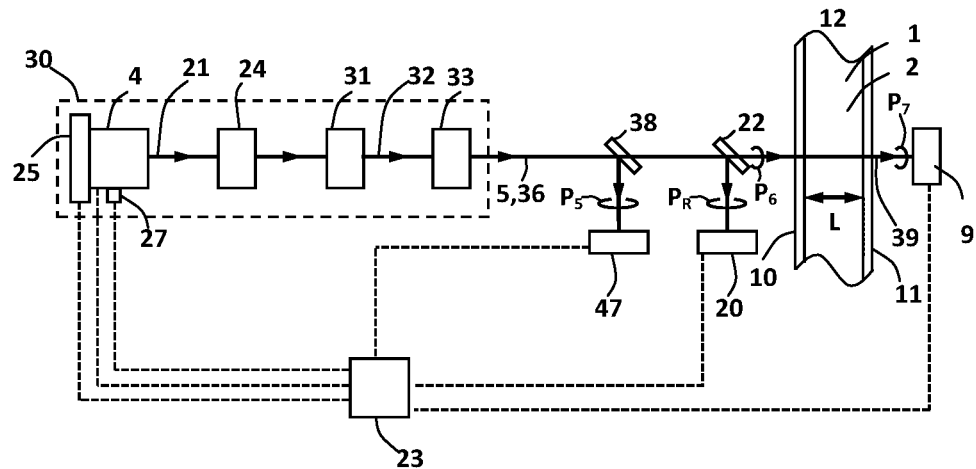
FIG. 20 shows an exemplary sensor device according to an aspect of the invention which uses the pump light to provide a measurement at a second wavelength.

A seventh example of the invention is now described and is illustrated in FIG. 20. The sensor device in the seventh example is similar to the sixth example. As for the sixth example some of the light with a first central wavelength that was emitted by the solid-state light emitter 4 is used as light for a secondary sensor which is used to improve the accuracy of the concentration of the target which is determined from the primary sensor. The light source 30 may be the same as the light source in the sixth example. The light source 30 is operated using two or more different operating conditions. The light emitted by the light source 30 includes light 36 with the first central wavelength (with power $P_a$) and light 5 with the second central wavelength (with power $P_b$). The ratio of $P_a/P_b$ is different for the two or more different operating conditions of the light source 30. For example, the two or more different operating conditions may include two or more different electrical currents supplied to the solid-state light emitter 4.

The different values of the ratio $P_a/P_b$ may be obtained by exploiting a nonlinear dependence of the power of frequency-converted light generated in the frequency-converting element 31 on the power of light 21 emitted by the solid-state light emitter 4. The power of the light 36 ($P_a$) is proportional to the power of the light 21. The power of the light 5 ($P_b$) is proportional to the power of the frequency-converted light generated in the frequency-converting element 31.

Figure 21:
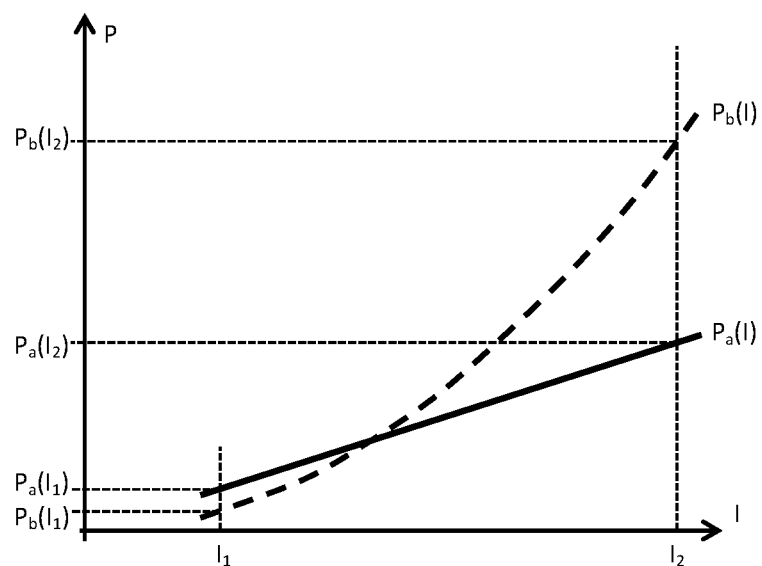
FIG. 21 shows the variation of optical power output for pump light $P_a$ and frequency-doubled light $P_b$ as a function of electrical current supplied to the pump wavelength emitter.

For example, the plot in FIG. 21 shows schematically a dependence of $P_a$ and $P_b$ on the electrical current supplied to the solid-state light emitter 4 in the light source 30. The power of the light with the first central wavelength ($P_a$) increases as the electrical current (I) is increased. In this example $P_a$ depends approximately linearly on the electrical current ($P_a \approx a_1 + a_2 I$, where $a_1$ and $a_2$ are constants), but this linear dependence is not essential for the present example. The power of light with the first central wavelength at a first electrical current ($I=I_1$) is lower than the power at a second electrical current ($I=I_2$; $I_2>I_1$): $P_a(I_1)<P_a(I_2)$. The power of the light with the second central wavelength ($P_b$) depends nonlinearly on the power of the light with the first central wavelength ($P_a$): $P_b \neq b_1 P_a$; where $b_1$ is a constant. In this specific example the dependence of $P_b$ on $P_a$ is: $P_b \approx b_2 \cdot P_a^2$ where $b_2$ is a constant. This approximate dependence is typical of a light source 30 which includes frequency-conversion by SHG. Other nonlinear dependencies of $P_b$ on $P_a$ may also be used.

Owing to the nonlinear dependence of $P_b$ on $P_a$, the ratio $P_a(I_1)/P_b(I_1)$ is different from the ratio $P_a(I_2)/P_b(I_2)$. For the example illustrated in FIG. 21, $P_a(I_1)/P_b(I_1)>P_a(I_2)/P_b(I_2)$. It is preferable that the light source 30 is configured such that $P_a(I_1)>h_1 P_b(I_1)$ and $P_b(I_2)>h_2 P_a(I_2)$ where $h_1 \geq 1$ and $h_2 \geq 1$. More preferably $h_1 \approx 2$ and/or $h_2 \approx 2$. More preferably still, $h_1 > 2$ and/or $h_2 > 2$.

The light 5 and the light 36 may propagate towards and through the analyte along similar optical paths, for example passing through windows 10, 11 at similar positions. After propagating through the analyte 2, the transmitted light 39, which includes light of the first central wavelength and of the second central wavelength is incident on the first photodetection means 9 (referring to FIG. 20). The power of the light incident on the first photodetection means is $P_7$, which is a sum of power of transmitted light with the first central wavelength ($P_4$) and transmitted light with a second central wavelength ($P_2$): $P_7=P_2+P_4$. The first photodetection means is used to determine $P_7$ for the at least two operating conditions of the light source 30. For example, two electrical currents: $P_7(I_1)$ and $P_7(I_2)$.

The power of the light incident on the analyte is $P_6$, which is a sum of power of light with the first central wavelength ($P_3$) and light with the second central wavelength ($P_1$): $P_6=P_1+P_3$. The values of $P_1$ and $P_3$ for the two or more operating conditions of the light source 30 may be determined for a particular light source. Subsequently, the measurements of $P_7$ for two or more operating conditions of the light source 30 may be used to determine separately the transmittance of light with the first wavelength and light with the second wavelength through the system and analyte, thereby delivering similar function to the "secondary" and "primary" sensors in previous examples.

A second photodetection means 20 may be used to determine a power $P_R$ which is proportional to $P_1$, as in previous examples. Light may be coupled towards the second photodetection means 20 by a mirror 22. Preferably the mirror 22 reflects some of the light with the second central wavelength, does not significantly reflect light with the first central wavelength, and transmits some of the light with the first central wavelength and with the second central wavelength. In this case the light incident on the second photodetection means is approximately proportional to $P_1$. Optionally a filter (e.g. a bandpass filter) may be used to reduce the amount of light with the first central wavelength which is incident on the second photodetection means 20.

A fourth photodetection means 47 may be used to determine a power $P_5$ which is proportional to $P_3$, as in previous examples. Light may be coupled towards the fourth 1photodetection means 47 by a mirror 38. Preferably the mirror 38 reflects some of the light with the first central wavelength, does not significantly reflect light with the second central wavelength, and transmits some of the light with the second central wavelength and with first central wavelength. In this case the light incident on the fourth photodetection means is approximately proportional to $P_3$. Optionally a filter (e.g. a bandpass filter) may be used to reduce the amount of light with the second central wavelength which is incident on the second photodetection means 47.

If the second and/or fourth photodetection means 20, 47 are used, the measurements of $P_R$ and/or $P_5$ for the two or more operating conditions of the light source 30 may be used in conjunction with the measurements of $P_7$ for the two or more operating conditions to improve the accuracy with which the transmittance of light with the first central wavelength and transmittance of light with the second central wavelength are determined.

Preferably, $P_a(I_1) \gg P_b(I_1)$ and $P_b(I_2) \gg P_a(I_2)$ so that the measurement using the first operating current ($I_1$) is dominated by the transmittance of light with the first central wavelength through the system and analyte (i.e. similar function to the "secondary sensor" in previous examples) and the measurement using the second operating current ($I_2$) is dominated by the transmittance of light with the second central wavelength (i.e. similar function to the "primary sensor" in previous examples).

By operating the light source 30 with two or more operating conditions (electrical currents in this example), the transmittance of light with the first central wavelength through the windows and analyte and the light with the second central wavelength through the windows and analyte may be determined. Therefore, the benefits of the sixth example may be obtained in device with fewer components (e.g. the third photodetection means is not required).

EXAMPLE 8

An eighth example of this invention is now described. In this eighth example, illustrated in FIG. 14, an additional photodetection means is added to measure a power of a light scattered by the analyte. This additional photodetection means may be added to a sensor device which is constructed according to any of the previous examples. Features which are common to the examples described previously will not be repeated here.

Figure 14:
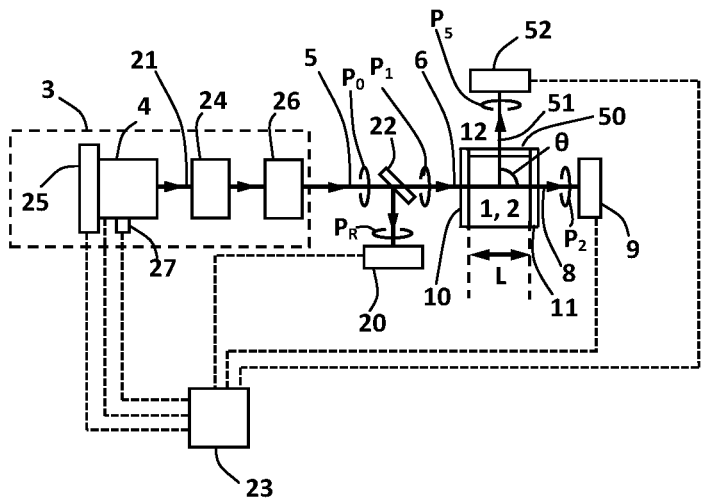
FIG. 14 shows an exemplary sensor device according to an aspect of the invention which includes a measurement of scattered light.

An additional window 50 may be included in the analyte-handling means 12 to allow light emitted by the light source 3, and which is scattered by the analyte 2 at an angle θ to the unscattered light 8, to be substantially transmitted out of the analyte-handling means 12. The window 50 fulfils the same criteria as for the windows 10, 11 and may be made from the same material. The scattered light 51 is coupled to at least one photodetection means 52 which has similar design considerations as for the photodetection means 9. The photodetection means may include one or more photodiodes located at one or more positions, thereby detecting light scattered in the analyte through one or more angles. One scattering angle, θ, is illustrated in FIG. 14 by way of example. The one or more scattering angles are chosen to be sufficiently large such that the transmitted light 8 does not impinge on the photodetection means 52. The angle θ may be between 5° and 180° and is preferably between 60° and 120°. The angle θ is more preferably approximately 90°.

The output from photodetection means 52 may be conveyed as an input to a controller by either wired or wireless means. The controller may be the same controller 23 which receives the signal from photodetection means 9. The power incident on the photodetection means 52 may be used to determine a property of the system or the analyte (e.g. the turbidity of the analyte) which may be used to improve the accuracy with which the concentration of the target in the analyte is determined by the sensor device. In a similar manner to that which was described in the fourth example this measurement may be used to obtain one of the terms $T_i$ in the equation for the transmitted fraction of the light power in the sensor device and increase the accuracy of with which the concentration of the target in the analyte is determined by the sensor device.

Corrections for fluctuations in the intensity of the light output by the light source 3 may be carried out using the optional photodetection means 20 in a similar manner as for the transmitted light 8 incident on the photodetection means 9 as described in the first example.

Advantageously this device uses only the light from the light source 3 to determine a property such as the turbidity of the analyte without necessarily needing a secondary light source 40.

It is preferable to use a light source 3 including a solid-state light emitter 4 which includes a laser (and, if a light source 30 including a frequency-converting element 31 is used as an alternative to the light source 3, it is preferable to include a solid-state light emitter 4 which is a laser). Use of a laser is advantageous because it provides incident light 6 which has a high beam quality and/or has a high degree of linear polarisation. Light scattered from incident light with high beam quality (e.g. "collimated" laser beam) can be effectively distinguished from the incident light by the location of the photodetection means 52. Light scattered from incident light with a high degree of linear polarisation can be effectively distinguished from the incident light because the scattered light may have random linear polarisation.

EXAMPLE 9

A ninth example of this invention is now described. This example describes an improvement which is made to the analyte-handling means 12 which may be advantageous for operation of a sensor device in some applications. The sensor system may be similar to any of those described in this disclosure and common features will not be repeated.

It is possible that during operation of the sensor the surface of the windows 10, 11 which are in contact with the analyte 2 may become coated with substances which absorb or scatter light emitted by any one of the light sources 3, 30, 40. These substances may include bacteria, salt deposits, organic molecules and other sources of dirt (e.g. soil, mud, clay, etc.). If this additional optical loss of the system (one of the factors $T_i$ described earlier in the Detailed Description) is not accounted for then an error will be introduced into the concentration of the target determined by the sensor device because the absorption will be erroneously attributed to the target 1. Therefore, it is desirable to keep the windows 10, 11 as free from these contaminating substances as possible, or in a state where the effect of contamination does not vary significantly. This may be achieved by the inclusion of a window-cleaning means in the analyte-handling means 12.

The window-cleaning means may include a wiper which physically contacts one or both of the surfaces of the windows 10, 11 which are in contact with the analyte. The wiper may include nitrile rubber, silicone or nylon, for example. The wiper is periodically driven across the surfaces of the windows 10, 11, including the entirety of the window surface through which the light from the light source 3 or the light source 30 propagates and which is in contact with the analyte 2. The wiper may be driven by an electrical motor. Alternatively, the wiper may be driven by a pneumatic or hydraulic system.

The window-cleaning means may include a nozzle supplied with a compressed fluid. The fluid may be air. Alternatively the fluid may be water. The nozzle is angled such that a jet of the fluid passes over either or both of the surfaces of the windows 10, 11, including the entirety of the window surface through which the light 6, 8 passes and which is in contact with the analyte 2.

The window-cleaning means may include one or more elements designed to vibrate either one or both of the windows 10, 11. For example the elements may be lead zirconate titanate (PZT) based materials driven at frequencies greater than 20 kHz to produce ultrasound. The one or more elements may be attached directly onto the windows 10, 11. Alternatively the one or more elements may be attached to any part of the sensor which is in physical contact with the windows 10, 11.

The interval between operation of the window-cleaning means may be set as desired by the user. For example, the window cleaning means may be operated every 1 minute, every 15 minutes, every hour or every day. Alternatively, the window cleaning means may be operated before the sensor device is used to obtain a measurement of the concentration of the target in the analyte. The window-cleaning means may be operated by optional controller 23. The window-cleaning means is preferably not operated while transmittance measurements are being taken by the sensor device.

EXAMPLE 10

Figure 15:
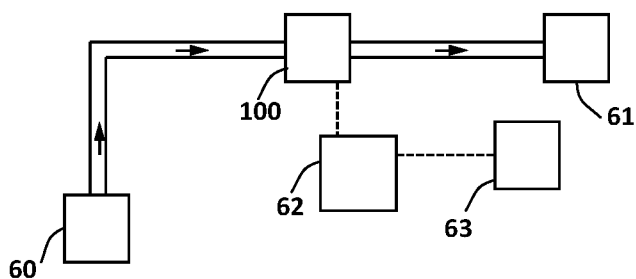
FIG. 15 shows a possible deployment of an exemplary sensor device in a drinking water system.

A tenth example of this invention is now described. This example is illustrated in FIG. 15. This example uses a sensor device constructed according to any of the previous examples to monitor the concentration of an ion, molecule or atom in an analyte and provide warning if the concentration rises above a first set limit value and/or below a second set limit value. This example is described with reference to a sensor device configured to measure nitrate ion concentration in water intended for human consumption.

The sensor device 100 is placed in-line with the drinking water supply between the water source 60 and one or more points of use 61. The drinking water supply may be a municipal drinking water treatment facility. The drinking water supply may be a ground-source water well. For example, the sensor device may be placed on the water pipe which carries drinking water at the point where it enters the house. Alternatively the sensor device may be placed in close proximity to a water tap, e.g. under a sink in a kitchen. Alternatively the sensor device may be located within a water treatment facility.

The result of the concentration measurement performed by the sensor device is compared to a first set limit value, such as the WHO 50 mg/liter upper limit on nitrate ion concentration in drinking water, by a controller 62. This comparison may be carried out within the sensor device, with the controller being the same optional controller 23. If the measurement is found to exceed the first set limit value then a signal is sent to activate an alarm 63, for example located near the one or more points of use 61, to warn the user that the water is unsafe to drink. The signal may be sent by wired or wireless means. The alarm may be an audible, visual or audio-visual alarm.

EXAMPLE 11

Figure 16:
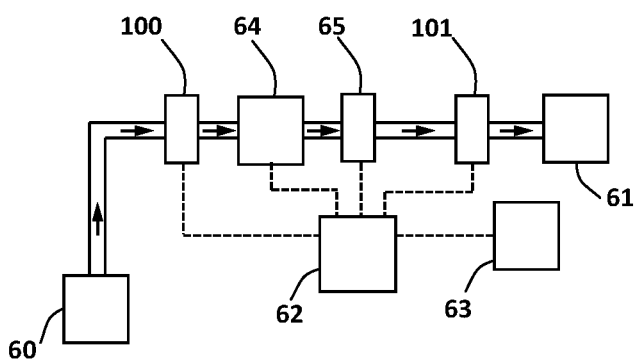
FIG. 16 shows a possible deployment of an exemplary sensor device with an automated concentration-adjusting means.

An eleventh example of this invention is now described. This eleventh example is illustrated in FIG. 16. This example uses one or more sensor devices 100, 101 configured according to any of the examples 1-9 to monitor the concentration of an ion, molecule or atom in an analyte and treat the analyte if the concentration lies outside a set range. Optionally, additional sensor devices 65 of types other than the disclosed invention may be used in combination with the one or more sensor devices 100, 101.

The one or more sensor devices 100, 101, 65 are disposed between an analyte source 60 and an analyte point of use 61. A first sensor device 100 may measure the concentration of a target in the analyte received from the analyte source 60. If the concentration of the target in the analyte, as determined by the first sensor device 100, is above a set limit value then a concentration adjusting means 64 is used to reduce the concentration of the target in the analyte before the analyte is provided to the point of use 61. Optionally a second sensor device 101 may measure the concentration of the target in the analyte provided to the point of use 61. The concentration measurements from the sensor devices 100, 101, 65 may be received by a controller 62 (e.g. a microprocessor or microcontroller) which controls the operation of the concentration adjusting means 64. The first and second sensor devices may be used to ensure that the concentration adjusting means is deployed appropriately to provide analyte to the point of use in which the target concentration is within a set range, and optimise the use of the concentration adjusting means (for example, to minimum energy use by the concentration adjusting means).

In a first deployment of this example the analyte is water, the analyte source 60 is a ground source well, the point of use 61 is a tap to supply water with a concentration of nitrate which is below a set value (e.g. the WHO 50 mg/liter upper limit), the sensor devices 100, 101 are sensors according to any one of examples 1-9 configured appropriately to measure this nitrate ion concentration in water, and the concentration adjusting means 64 is a reverse osmosis water purifier, an ion exchange water purifier, or another purifier which can reduce the concentration of nitrate in water. The concentration of nitrate in water determined by the sensor devices 100, 101 is used to ensure that the water provided to the point of use 61 has a nitrate ion concentration below the set value and the concentration measurements are used to ensure that the concentration adjusting means is not used unnecessarily (for example if the nitrate concentration in the water received from the analyte source 60 is already below the set value). This deployment provides a source of drinking water where the cost of energy and consumables to operate a concentration adjusting means (e.g. reverse osmosis, ion exchange) is minimised. Optionally an alarm 63 may be included, similar to the tenth example, to warn if the nitrate concentration in the water supplied to the point of use 61 is above the set value, for example due to failure of the concentration adjusting means 64.

In a second deployment of this example the analyte is water is a recirculating aquaculture system (RAS) in which the nitrate ion concentration in the recirculating water is to be maintained below a set value. The analyte source 60 is water received from a tank containing fish or other aquatic organisms (either directly or via a holding tank), the point of use 61 is water returned to a tank containing fish or other aquatic organisms (either directly or via a holding tank), the sensor device 100, 101 are sensors according to any one of the examples 1-9 configured to measure the concentration of nitrate ions in water, and the concentration adjusting means 64 includes an inlet from a separate water source. The separate water source provides water with a lower nitrate ion concentration than the set value for nitrate ion concentration. Thereby the addition of water from the separate water source to the water received from the analyte source 60 can reduce the concentration of nitrate ions in the water provided to the point of use 61. The concentration of nitrate ions in the water determined by the sensor device 100, 101 is used to ensure that the water provided to the point of use has a nitrate ion concentration below the set value. The concentration measurements are used to ensure that the concentration adjusting means 64 is not used unnecessarily. For example, water from the separate water source is not added to the water received from the analyte source unless necessary. This deployment provides a RAS system in which the nitrate ion concentration is maintained below a set value (for example, to ensure productive growth of fish) while minimising energy and water use associated with addition of water from a separate water source. This can be especially advantageous if water is scarce or if the water must be heated and/or sterilised before it can be added to the RAS system. The water may be seawater. The sensor devices 100, 101 may be combined with other sensors 65 monitoring the concentration of other ions, elements or molecules in the water.

In a third deployment of this example the analyte is water supplied to plants in an agricultural facility, for example water supplied to plants grown by hydroponics, aquaponics or aeroponics. For the remainder of this deployment hydroponic plant growth is used as an example and the nitrate ion concentration is to be maintained between a lower and upper limit. The analyte source 60 is water received from the plants being grown (either directly or via a holding tank), the point of use 61 is water returned to the plants being grown (either directly or via holding tank), the sensor device 100, 101 are sensors according to any of the examples 1-9 configured to measure the concentration of nitrate in water, and the concentration adjusting means 64 includes one or more inlets from one or more tanks containing stock nutrient solution. The one or more stock nutrient solutions may include a source of nitrate ions, such as ammonium nitrate or potassium nitrate. Therefore the concentration of nitrate ions in the water at the point of use 61 compared to the water received from the analyte source 60 may be increased or decreased by increasing or decreasing the rate of addition of one or more nitrate ion-containing nutrient solutions to the water respectively. The concentration of nitrate ions in the water determined by the sensor device 100, 101 is used to ensure that the water provided to the point of use has a nitrate ion concentration within the specified range. The concentration measurements are used to optimise the addition of stock nutrient solution to the water. One or more optional sensor devices 65 may be included, such as a pH sensor and/or an electrical conductivity (EC) sensor. The controller 62 may use the information provided by these optional additional sensors to further optimise the rates of addition of other nutrient stock solutions in response to changes caused by altering the rate of addition of one or more nitrate ion-containing nutrient solutions. This deployment provides a hydroponic system in which the nitrate ion concentration in the water is maintained within a set range while both minimising use of stock nutrient solution (reducing operating costs) and ensuring a sufficient supply of nitrate ions to the plants (optimising yields and maximising profits).

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

A sensor device according to the current invention may be used to measure the concentration of ions such as nitrate ion in water. The sensor device may be used in a device to determine if water is unsafe for human consumption. The sensor device may be used to optimise wastewater treatment processes. The sensor device may also be used in a device to determine if water is detrimental to the health of fish in fish farms due to high nitrate ion concentration, facilitating improved yields. The sensor device may also be used in a device used to determine if the concentration of nitrate ions in water is at an optimal level for plant growth in a hydroponic farm, facilitating improved yields.

What is claimed is:

1. A sensor for measuring a concentration of one or more types of ions, molecules or atoms in a fluid, comprising:
   at least one photo-detection device configured to measure a power of light incident thereon;
   a first light source including a solid-state light emitting device, the first light source configured to emit light having a wavelength less than 240 nanometers incident on the fluid, and the at least one photo-detection device configured to receive light having passed through the fluid; and
   a second light source including a solid-state light emitting device, the second light source configured to emit light having a wavelength less than 240 nanometers, different from the wavelength emitted by the first light source, incident on the fluid, the at least one photo-detection device configured to receive light having passed through the fluid,
   wherein a spectral linewidth of at least one of the first and second light sources is less than 2 nanometers.

2. The sensor according to claim 1, where the at least one photo-detection device comprises a first photo-detection device and a second photo-detection device, and wherein the first photo-detection device is configured to receive light from the first light source having passed through the fluid, and the second photo-detection device is configured to receive light from the second light source having passed through the fluid.

3. The sensor according to claim 1, wherein the first and second light sources each comprise a frequency converting element arranged to receive light emitted from the respective solid-state light emitting device, the frequency converting element configured to convert the light emitted by the respective solid-state light emitting device to frequency-converted light with a wavelength less than 240 nanometers.

4. The sensor according to claim 3, wherein a frequency conversion process of the frequency conversion element is one of second harmonic generation, third harmonic generation, fourth harmonic generation, fifth harmonic generation, sum frequency-generation or difference frequency-generation and the frequency-conversion process is not phase-matched for frequency-converted light with wavelengths less than a first wavelength and greater than a second wavelength.

5. The sensor according to claim 1, wherein one type of ion, molecule or atom is a nitrate ion and another type of ion, molecule or atom is a nitrite ion.

6. The sensor according to claim 1, wherein the first and second light sources are the same light source operated under different operating conditions.

7. The sensor according to claim 6, wherein the operating condition that is changed is at least one of an ambient temperature, a temperature of the first light source, or a current provided to the first light source.

8. The sensor according to claim 1, further comprising a controller operatively coupled to the first photo-detection device, the controller configured to determine the concentration of the one or more types of ions, molecules or atoms in the fluid based on a transmittance through the fluid of light emitted by the first light source.

9. The sensor according to claim 8, wherein the controller is operatively coupled to the second photo-detection device and configured to determine the transmittance through the fluid of light emitted by the first light source based on the ratio $P_2/P_1$, where $P_2$ is the power of light passing through the fluid and incident on the first photo-detection device and $P_1$ is the power of the light incident on the fluid, $P_1$ and $P_2$ based on data provided by the second and first photo-detection devices, respectively.

10. The sensor according to claim 1, further comprising a sample handling portion for providing at least some of the fluid.

11. The sensor according to claim 1, further comprising at least one additional photo-detection device configured to measure a power of light incident thereon, the at least one additional photo-detection device arranged to receive light scattered by the fluid.

12. The sensor according to claim 1, wherein the solid-state light emitting device comprises at least one of a solid state light emitting device comprised of $Al_yIn_xGa_{1-y-x}N$ semiconductor materials, where $0 \leq y \leq 1$; $0 \leq x = 1$, a light-emitting diode, a semiconductor laser, or a laser diode.

13. The sensor according to claim 1, further comprising a stabilizing device configured to stabilize a wavelength of light emitted by the respective solid-state light emitting device.

14. The sensor according to claim 13, wherein the stabilizing device comprises at least one of a diffraction grating, a dichroic mirror, a temperature control device configured to regulate a temperature of the light emitting device, a wavelength filter, a current regulator configured to regulate a current provided to the light emitting device, or a voltage regulator configured to regulate a voltage applied to the light emitting device.

15. The sensor according to claim 1, further comprising a wavelength sensor configured to provide data indicative of a wavelength of the light emitted by at least one of the first light source or the second light source.

16. The sensor according to claim 15, wherein the wavelength sensor comprises at least one of a temperature sensor configured to measure a temperature of the first light source or the second light source, a current sensor configured to measure a current provided to the first light source or the second light source, or a spectrophotometer.

17. The sensor according to claim 1, wherein the frequency converting element comprises a crystal of $\beta\text{-BaB}_2\text{O}_4$, $\text{Ba}_{1-x}\text{B}_{2-y-z}\text{O}_4\text{—Si}_x\text{Al}_y\text{Ga}_z$ ($0 \leq x \leq 0.15$; $0 \leq y \leq 0.10$; $0 \leq 0 \leq 0.04$; $x+y+z \neq 0$), $\text{SiO}_2$, $\text{Al}_y\text{Ga}_{1-y}\text{N}$ ($0.5 \leq y \leq 1$), $\text{CsLiB}_6\text{O}_{10}$, $\text{LiB}_3\text{O}_5$, $\text{KBe}_2\text{BO}_3\text{F}_2$, $\text{Li}_2\text{B}_4\text{O}_7$, $\text{LiRbB}_4\text{O}_7$, or $\text{MgBaF}_4$.

18. The sensor according to claim 1, wherein the first light source is configured to emit light with a spectral bandwidth of less than 2 nanometers.

19. A system for monitoring a concentration of one or more types of ions, molecules or atoms in a fluid, comprising:
the sensor according to claim 1; and
at least one of an alarm device operatively coupled to the sensor or a concentration variation device operatively coupled to a controller which is operatively coupled to the sensor;
wherein the alarm device is configured to generate an output indicative of a concentration of the one or more types of ions, molecules or atoms in the fluid falling outside a prescribed concentration;
and wherein the concentration variation device is configured to vary the concentration of the one or more types of ions, molecules or atoms in the fluid and the controller is configured to control operation of the concentration variation device based on data from the sensor.

* * * * *